United States Patent [19]

Lidert et al.

[11] Patent Number: 5,530,028
[45] Date of Patent: Jun. 25, 1996

[54] INSECTICIDAL N'-SUBSTITUTED-N,N'-DIACYLHYDRAZINES

[75] Inventors: Zev Lidert, Doylestown; Dat P. Le, North Wales; Robert E. Hormann, Philadelphia; Thomas R. Opie, North Wales, all of Pa.

[73] Assignee: Rohm and Haas Company, Philadelphia, Pa.

[21] Appl. No.: 129,549

[22] Filed: Sep. 29, 1993

Related U.S. Application Data

[63] Continuation-in-part of Ser. No. 984,189, Nov. 23, 1992, Pat. No. 5,344,958.

[51] Int. Cl.$^6$ .................. A01N 33/26; C07C 243/16; C07C 243/38
[52] U.S. Cl. .................. 514/649; 514/664; 564/310; 564/311; 549/366; 549/436; 549/405
[58] Field of Search .................. 514/100, 101, 514/649, 664, 366; 549/436, 405; 564/310, 311

[56] References Cited

U.S. PATENT DOCUMENTS

| | | | |
|---|---|---|---|
| 4,161,611 | 7/1979 | Kim | 562/474 |
| 4,389,401 | 6/1983 | Smolanoff | 424/248.56 |
| 4,954,655 | 9/1990 | Kelly | 564/464 |
| 4,985,461 | 1/1991 | Hsu et al. | 514/615 |
| 5,110,979 | 5/1992 | Nguyen | 560/61 |
| 5,110,986 | 5/1992 | Kelly | 564/149 |
| 5,117,057 | 5/1992 | Hsu et al. | 564/149 |
| 5,378,726 | 1/1995 | Yanagi et al. | 514/456 |

FOREIGN PATENT DOCUMENTS

| | | |
|---|---|---|
| 401125 | 12/1990 | European Pat. Off. |
| 496342 | 7/1992 | European Pat. Off. |
| 5039252 | 2/1993 | Japan. |

OTHER PUBLICATIONS

Chemical Abstract 136332: vol. 81, p. 441, 1974.
Meyers, et al., pp. 3881–3886, 1961, "Chemistry of Aryloxazolines", J. Org. Chem. vol. 46.
Fringuelli, et al., pp. 4249–4256, 1969, "Synthesis of Methyl (±)-7-oxo-8-methyl-podocarb-8-en-16-oate", Tetrahedron, vol. 25.
Cresp et al., pp. 2435–2447, 1974 "Synthesis of Piloquinone . . . ", J. Chem. Soc. Perkin Trans. I, vol. 21.
McAlees, pp. 2030–2036, 1977, "Hydrogenation of Substituted Phthalic Anhydrides . . . ", J. Chem. Soc. Perkin Trans. I.
Meyers, et al., pp. 7383–7385, 1975, "Oxazolines XXIII . . . " J. Amer. Chem. Soc. 97:25.
Meyers, et al., 1372–1379, 1977 "Nucleophillic Aromatic Substitution . . . ", J. Org. Chem., vol. 43, No. 7.
Campbell, pp. 3963–3966, 1986, "Metallation of Rigid 2-aryl-1,3-Dioxanes", J. Tetrahedron Letters, vol. 27, No. 34.
Rathi, et al., pp. 4006–4010, 1989, "Repetitive Imidazole Synthesis . . . ". J. Org. Chem. vol. 55.
Tanaka, et al., pp. 553–559, 1989 "Identification of the Isomeric Hydroxylated Metabolites . . . ", J. Agric. Food Chem., vol. 38.
Vogel, pp. 924–925, 1978, Textbook of Practical Organic Chemistry.

Primary Examiner—Richard L. Raymond
Assistant Examiner—Brian G. Bembenick
Attorney, Agent, or Firm—Clark R. Carpenter

[57] ABSTRACT

Insecticidal compounds having the formula N-(2-$R^a$-3-$R^b$-4-$R^h$-benzoyl)-N'-(2-$R^c$-3-$R^d$-4-$R^e$-5-$R^f$-benzoyl)-N'-$R^g$-hydrazine wherein $R^a$ is a halo or lower alkyl; Rb is lower alkoxy, optionally substituted with halo (preferably fluoro); $R^c$ is selected from hydrogen, halo, lower alkyl, lower alkoxy, lower alkoxy lower alkyl, and nitro; $R^d$, $R^e$ and $R^f$ are each independently selected from hydrogen, bromo, chloro, fluoro, lower alkyl, lower alkoxy, and lower alkoxy lower alkyl; $R_g$ is a ($C_4$–$C_6$)alkyl; $R^h$ is hydrogen, lower alkoxy, lower alkyl, or when taken together with $R^b$ is methylenedioxy (—OCH$_2$O—), 1,2-ethylenedioxy (—OCH$_2$CH$_2$O—), 1,2-ethyleneoxy (—CH$_2$CH$_2$O—) or 1,3-propyleneoxy (—CH$_2$CH$_2$CH$_2$O—) wherein an oxo atom is located at the $R^b$ position; and the substituents $R^c$ and $R^d$, or $R^d$ and $R^e$, or $R^e$ and $R^f$ when taken together can be methylenedioxy or 1,2-ethylenedioxy as well as compositions comprising an agronomically acceptable carrier and an insecticidally effective amount of such compounds; and methods of using such compounds and compositions.

Also, methods for the production of the compounds and their intermediates, which methods comprise either admixing a 3-amino-2-(substituted)-benzoic acid, sodium nitrite and methanol under acidic conditions or admixing a 3,4-fused heterocyclic benzoic acid and an alkyl lithium reagent followed by subsequent reaction with an electrophilic reagent.

31 Claims, No Drawings

INSECTICIDAL N'-SUBSTITUTED-N,N'-DIACYLHYDRAZINES

This application is a continuation-in-part of application Ser. No. 07/984,189, filed Nov. 23, 1992 (U.S. Pat. No. 5,344,958).

BACKGROUND OF THE INVENTION

This invention relates to N'-substituted-N,N'-diacylhydrazines which are useful as insecticides, compositions containing those compounds and methods of their use. This invention also relates to the production of intermediates useful in the production of such compounds.

The search for compounds which have a combination of excellent insecticidal activity and low undesirable toxicity is a continuing one because of factors such as the desire for compounds exhibiting greater activity, better selectivity, lower undesirable environmental impact, lower production and market cost and higher effectiveness against insects which are or become resistant to many known insecticides.

Prior processes for the production of the 3-alkoxy-2-alkylbenzoic acid intermediates, useful in the production of some of the N'-substituted-N,N'-diacylhydrazines of the present invention have the production of 3-hydroxy-2-alkylbenzoic acid compounds from hydrochloride salt of 2-alkyl-3-aminobenzoic acid as a preceding step. Such exothermic anilinium hydrochloride salt reactions pose reaction safety and substance stability concerns and require controlled cooling. Such constraints can create safety and cost burdens on the production of the useful intermediates concerned herein.

Furthermore, prior processes for the production of 2-alkyl-3,4-alkylenedioxybenzoic acid intermediates useful in the production of some of the other N'-substituted-N,N'-diacylhydrazines of the present invention involve the use of activating/protecting groups in place of the carboxy group and require extra steps for conversion to the benzoic acid.

There continues to be a need to develop insecticidal compounds having improved insecticidal and methods of production properties as described above. There also continues to be a need to develop safened processes for the production of the intermediate compounds useful in such methods. The present invention provides improved N'-substituted-N,N'-diacylhydrazines which are unexpectedly propertied with enhanced, higher activity as well as a safened method for production of intermediates useful for their production. The combination of higher activity, better economics of manufacture, and safer production methods can provide an economic and environmental advantage in the use of the inventive compounds.

SUMMARY OF THE INVENTION

In accordance with the present invention, there are provided insecticidal compounds having the formula N-(2-$R^a$-3-$R^b$-4-$R^h$-benzoyl)-N'-(2-$R^c$- 3-$R^d$-4-$R^e$-5-$R^f$-benzoyl)-N'-$R^g$-hydrazine which may be depicted structurally as follows:

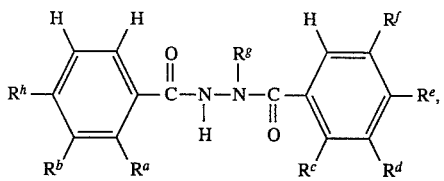

wherein $R^a$ is a halo or lower alkyl; $R^b$ is lower alkoxy, optionally substituted with halo (preferably fluoro); $R^c$ is selected from hydrogen, halo, lower alkyl, lower alkoxy, lower alkoxy lower alkyl, and nitro; $R^d$, $R^e$ and $R^f$ are each independently selected from hydrogen, bromo, chloro, fluoro, lower alkyl, lower alkoxy, and lower alkoxy lower alkyl; $R_g$ is a branched ($C_4$–$C_6$)alkyl; $R^h$ is hydrogen, lower alkoxy, lower alkyl, or when taken together with $R^b$ is methylenedioxy (—$OCH_2O$—), 1,2-ethylenedioxy (—$OCH_2CH_2O$—), 1,2-ethyleneoxy (—$CH_2CH_2O$—) or 1,3-propyleneoxy (—$CH_2CH_2CH_2O$—) wherein an oxo atom is located at the $R^b$ position; and the substituents $R^c$ and $R^d$, or $R^d$ and $R^e$, or $R^e$ and $R^f$ when taken together can be methylenedioxy or 1,2-ethylenedioxy.

Also provided are compositions comprising an agronomically acceptable carrier and an insecticidally effective amount of such compounds; and methods of using such compounds and compositions. The compounds and compositions of the present invention are insecticidally active against insects of the order Lepidoptera. Certain of these compounds and compositions are distinguished by their insecticidal activity against insects of both the orders Lepidoptera and Homoptera.

Also described are improved methods for safer and more direct production of the compounds and their intermediates, which methods comprise effectively admixing a 3-amino-2-(substituted)benzoic acid, sodium nitrite and an alcohol under acidic conditions to produce a reaction mass predominantly comprising a 3.-alkoxy-2-(substituted)benzoic acid.

Additionally described are improved methods for more direct production of certain 2-alkyl-3,4-fused heterocyclic benzoic acids and 2-halo-3,4-fused heterocyclic benzoic acids which are intermediates of some insecticidal compounds described herein. The method comprises effectively admixing a 3,4-fused heterocyclic benzoic acid and an alkyl lithium reagent followed by subsequent reaction with an electrophilic reagent.

DETAILED DESCRIPTION OF THE INVENTION

Halo is chloro, fluoro, bromo or iodo.

Lower alkyl is straight chain or branched ($C_1$–$C_6$)alkyl such as methyl, ethyl, n-propyl, isopropyl, n-butyl, isobutyl, sec-butyl, tert-butyl, n-amyl, isoamyl, neopentyl, n-hexyl, isohexyl, methylneopentyl (3,3-dimethyl-2-butyl) and the like.

Lower alkoxy is a straight chain or branched ($C_1$–$C_4$)alkoxy, optionally substituted with halo, such as methoxy, ethoxy, n-propoxy, isopropoxy, n-butoxy, isobutoxy, trifluoromethoxy, difluoromethoxy and the like.

Lower alkoxy lower alkyl is a ($C_1$–$C_4$)alkoxy($C_1$–$C_3$)alkyl such as methoxymethyl, ethoxymethyl, 2-methoxyethyl, 2-ethoxyethyl and the like.

One embodiment of the present invention is an insecticidal compound having a formula of N-(2-$R^a$-3-$R^b$-4-$R^h$-benzoyl)-N'-(2-$R^c$-3-$R^d$-4-$R^e$-5-$R^f$-benzoyl)-N'-$R^g$-hydrazine, wherein $R^a$ is a halo, preferably bromo or chloro, or lower alkyl, preferably a ($C_1$–$C_3$)alkyl, more preferably methyl or ethyl; $R^b$ is lower alkoxy, preferably a ($C_1$–$C_4$)alkoxy, more preferably methoxy, trifluoromethoxy or ethoxy, most preferably methoxy or ethoxy; $R^c$ is selected from hydrogen, bromo, chloro, fluoro, lower alkyl (preferably a ($C_1$–$C_3$)alkyl, more preferably methyl), lower alkoxy (preferably a ($C_1$–$C_4$)alkoxy, more preferably methoxy), ($C_1$–$C_2$)alkoxy($C_1$–$C_2$)alkyl (preferably methoxymethyl), and nitro; $R^d$, $R^e$ and $R^f$ are each independently selected from hydrogen, bromo, chloro, fluoro, lower alkyl (preferably a $(C_1-C_3)$alkyl, more preferably methyl), lower alkoxy (preferably a $(C_1-C_4)$alkoxy, more preferably methoxy) and $(C_1-C_2)$alkoxy$(C_1-C_2)$alkyl (preferably methoxymethyl); $R_g$ is a $(C_4-C_6)$alkyl, preferably tert-butyl, neopentyl or methylneopentyl, more preferably tert-butyl; $R^h$ is hydrogen, lower alkoxy (preferably a $(C_1-C_2)$alkoxy, lower alkyl (preferably a $(C_1-C_2)$alkyl), or when taken together with $R^b$ is methylenedioxy, 1,2-ethylenedioxy, 1,2-ethyleneoxy or 1,3-propyleneoxy wherein an oxo atom is located at the $R^b$ position; and the substituents $R^c$ and $R^d$, or $R^d$ and $R^e$, or $R^e$ and $R^f$ when taken together can be methylenedioxy or 1,2-ethylenedioxy. Structural representation of the embodied compounds can be made as follows:

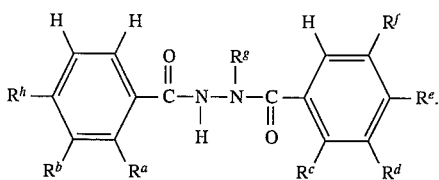

Preferred insecticidal compounds are those wherein $R^b$ is methoxy and $R^h$ is hydrogen or when $R^b$ and $R^h$ taken together are methylenedioxy or 1,2-ethylenedioxy, and $R^g$ is tert-butyl. More preferred are those wherein $R^a$ is methyl, ethyl, chloro or bromo, $R^b$ is methoxy and $R^h$ is hydrogen or when $R^b$ and $R^h$ taken together are methylenedioxy or 1,2-ethylenedioxy, $R^g$ is tert-butyl, and wherein no more than three of $R^c$, $R^d$, $R^e$ and $R^f$ are the same member selected from a group consisting of bromo, fluoro and chloro or no more than two of $R^d$, $R^e$ and $R^f$ are methoxy. The more preferred compounds are those wherein no more than three of $R^c$, $R^d$, $R^e$ and $R^f$ are independently selected from chloro, fluoro, methyl and methoxy with the remaining $R^c$, $R^d$, $R^e$ and $R^f$ being hydrogen. Most preferably, $R^d$ and $R^f$ are independently selected from chloro, methyl and methoxy and $R^c$ and $R^e$ are both hydrogen.

Preferred compounds because of their higher activity and/or better economics of production include:

N-(3-methoxy-2-methylbenzoyl)-N'-(3-chloro-5-methylbenzoyl)-N'-tert-butylhydrazine,
N-(3-methoxy-2-methylbenzoyl)-N'-(3,5-dimethylbenzoyl)-N'-tert-butylhydrazine,
N-(3-methoxy-2-methylbenzoyl)-N'-(3,5-dichlorobenzoyl)-N'-tert-butylhydrazine,
N-(3-methoxy-2-methylbenzoyl)-N'-(2,4-dichlorobenzoyl)-N'-tert-butylhydrazine,
N-(3-methoxy-2-methylbenzoyl)-N'-(3-methylbenzoyl)-N'-tert-butylhydrazine,
N-(3-methoxy-2-methylbenzoyl)-N'-benzoyl-N'-tert-butylhydrazine,
N-(3-methoxy-2-methylbenzoyl)-N'-(4-chlorobenzoyl)-N'-tert-butylhydrazine,
N-(3-methoxy-2-methylbenzoyl)-N'-(3,4,5-trichlorobenzoyl)-N'-tert-butylhydrazine,
N-(3-methoxy-2-methylbenzoyl)-N'-(3,4-dichlorobenzoyl)-N'-tert-butylhydrazine,
N-(3-methoxy-2-methylbenzoyl)-N'-(3-methoxy-5-methylbenzoyl)-N'-tert-butylhydrazine,
N-(3-methoxy-2-methylbenzoyl)-N'-(4-fluorobenzoyl)-N'-tert-butylhydrazine,
N-(3-methoxy-2-methylbenzoyl)-N'-(3-methoxy-4-methylbenzoyl)-N'-tert-butylhydrazine,
N-(3-methoxy-2-methylbenzoyl)-N'-(3,4-dimethylbenzoyl)-N'-tert-butylhydrazine,
N-(3-methoxy-2-methylbenzoyl)-N'-(3-methoxybenzoyl)-N'-tert-butylhydrazine,
N-(3-methoxy-2-methylbenzoyl)-N'-(4-chloro-3-methylbenzoyl)-N'-tert-butylhydrazine,
N-(3-methoxy-2-methylbenzoyl)-N'-(4-chloro-2-methoxybenzoyl)-N'-tert-butylhydrazine,
N-(3-methoxy-2-methylbenzoyl)-N'-(3-bromo-5-methylbenzoyl)-N'-tert-butylhydrazine,
N-(3-methoxy-2-methylbenzoyl)-N'-(3-bromo-5-chlorobenzoyl)-N'-tert-butylhydrazine,
N-(3-methoxy-2-methylbenzoyl)-N'-(3,5-difluorobenzoyl)-N'-tert-butylhydrazine,
N-(3-methoxy-2-methylbenzoyl)-N'-(4-methylbenzoyl)-N'-tert-butylhydrazine,
N-(3-methoxy-2-methylbenzoyl)-N'-(3-chloro-4-fluorobenzoyl)-N'-tert-butylhydrazine,
N-(3-methoxy-2-methylbenzoyl)-N'-(3-fluorobenzoyl)-N'-tert-butylhydrazine,
N-(3-methoxy-2-methylbenzoyl)-N'-(3,4-difluorobenzoyl)-N'-tert-butylhydrazine,
N-(3-methoxy-2-methylbenzoyl)-N'-(2-methoxy-4-methylbenzoyl)-N'-tert-butylhydrazine,
N-(3-ethoxy-2-methylbenzoyl)-N'-(3,5-dimethylbenzoyl)-N'-tert-butylhydrazine,
N-(3-methoxy-2-methylbenzoyl)-N'-(3-chlorobenzoyl)-N'-tert-butylhydrazine,
N-(3-methoxy-2-methylbenzoyl)-N'-(2-chloro-5-methylbenzoyl)-N'-tert-butylhydrazine,
N-(2-bromo-3-methoxybenzoyl)-N'-(3,5-dimethylbenzoyl)-N'-tert-butylhydrazine,
N-(2-chloro-3-methoxybenzoyl)-N'-(3,5-dimethylbenzoyl)-N'-tert-butylhydrazine,
N-(2-methyl-3-trifluoromethoxybenzoyl)-N'-(3,5-dimethylbenzoyl)-N'-tert-butylhydrazine,
N-(3-methoxy-2-methylbenzoyl)-N'-(3-bromo-4-fluorobenzoyl)-N'-tert-butylhydrazine,
N-(3-methoxy-2-methylbenzoyl)-N'-(4-fluoro-3-methylbenzoyl)-N'-tert-butylhydrazine,
N-(3-methoxy-2-methylbenzoyl)-N'-(3-chloro-4-methylbenzoyl)-N'-tert-butylhydrazine,
N-(3-methoxy-2-methylbenzoyl)-N'-(3-chloro-4-methoxybenzoyl)-N'-tert-butylhydrazine,
N-(3-methoxy-2-methylbenzoyl)-N'-(3-ethylbenzoyl)-N'-tert-butylhydrazine,
N-(3-methoxy-2-methylbenzoyl)-N'-(2,5-dichloro-4-fluorobenzoyl)-N'-tert-butylhydrazine,
N-(2-ethyl-3-methoxybenzoyl)-N'-(3,5-dimethylbenzoyl)-N'-tert-butylhydrazine,
N-(2-ethyl-3-methoxybenzoyl)-N'-(3-chloro-5-methylbenzoyl)-N'-tert-butylhydrazine,
N-(2-ethyl-3-methoxybenzoyl)-N'-(2-methoxybenzoyl)-N'-tert-butylhydrazine,
N-(2-ethyl-3-methoxybenzoyl)-N'-(2,5-difluorobenzoyl)-N'-tert-butylhydrazine,
N-(2-ethyl-3-methoxybenzoyl)-N'-(3-methoxybenzoyl)-N'-tert-butylhydrazine,
N-(2-ethyl-3-methoxybenzoyl)-N'-(3-methylbenzoyl)-N'-tert-butylhydrazine,
N-(2-ethyl-3-methoxybenzoyl)-N'-(3,5-dichlorobenzoyl)-N'-tert-butylhydrazine,
N-(2-ethyl-3-methoxybenzoyl)-N'-(2,4-dichlorobenzoyl)-N'-tert-butylhydrazine,
N-(2-ethyl-3-methoxybenzoyl)-N'-(2-chloro-5-methylbenzoyl)-N'-tert-butylhydrazine,
N-(2-methyl-3,4-methylenedioxybenzoyl)-N'-(3,5-dimethylbenzoyl)-N'-tert-butylhydrazine,
N-(2-ethyl-3,4-methylenedioxybenzoyl)-N'-(3,5-dimethylbenzoyl)-N'-tert-butylhydrazine, N-(2-chloro-3,4-methylenedioxybenzoyl)-N'-(3,5-dimethylbenzoyl)-N'-tert-butylhydrazine,
N-(2-bromo-3,4-methylenedioxybenzoyl)-N'-(3,5-dimethylbenzoyl)-N'-tert-butylhydrazine,
N-(3-ethoxy-2-ethylbenzoyl)-N'-(3,5-dimethylbenzoyl)-N'-tert-butylhydrazine,
N-(3,4-(1,2-ethylenedioxy)-2-methylbenzoyl)-N'-(3,5-dimethylbenzoyl)-N'-tert-butylhydrazine, and
N-(2-ethyl-3,4-(1,2-ethylenedioxy)benzoyl)-N'-(3,5-dimethylbenzoyl)-N'-tert-butylhydrazine.

Preferred insecticidal compounds wherein $R^g$ is $(C_5-C_6)$alkyl are those wherein $R^g$ is neopentyl or substituted neopentyl, preferably unsubstituted neopentyl, or methylneopentyl. Preferred neopentyl compounds are N-(3-methoxy-2-methylbenzoyl)-N'-(3,5-dimethylbenzoyl)-N'-neopentylhydrazine, N-(3-methoxy2-methylbenzoyl)-N'-(3,5-dimethylbenzoyl)-N'-(methylneopentyl)hydrazine, N-(3-methoxy-2-ethylbenzoyl)-N'-(3,5-dimethylbenzoyl)-N'-neopentylhydrazine and N-(3-methoxy-2-ethylbenzoyl)-N'-(3,5-dimethylbenzoyl)-N'-(methylneopentyl)hydrazine.

More preferred compounds and compositions thereof because of their superior insecticidal activity against insects of the order Lepidoptera include:

N-(3-methoxy-2-methylbenzoyl)-N'-(3-chloro-5-methylbenzoyl)-N'-tert-butylhydrazine,
N-(3-methoxy-2-methylbenzoyl)-N'-(3,5-dimethylbenzoyl)-N'-tert-butylhydrazine,
N-(3-methoxy-2-methylbenzoyl)-N'-(3-methylbenzoyl)-N'-tert-butylhydrazine,
N-(3-methoxy-2-methylbenzoyl)-N'-(3,5-dichlorobenzoyl)-N'-tert-butylhydrazine,
N-(3-methoxy-2-methylbenzoyl)-N'-(3,4-dichlorobenzoyl)-N'-tert-butylhydrazine,
N-(3-methoxy-2-methylbenzoyl)-N'-(3-methoxy-5-methylbenzoyl)-N'-tert-butylhydrazine,
N-(3-methoxy-2-methylbenzoyl)-N'-(4-fluorobenzoyl)-N'-tert-butylhydrazine,
N-(3-methoxy-2-methylbenzoyl)-N'-(3-methoxy-4-methylbenzoyl)-N'-tert-butylhydrazine,
N-(3-methoxy-2-methylbenzoyl)-N'-(3,4-dimethylbenzoyl)-N'-tert-butylhydrazine,
N-(3-methoxy-2-methylbenzoyl)-N'-(3-methoxybenzoyl)-N'-tert-butylhydrazine,
N-(3-methoxy-2-methylbenzoyl)-N'-(4-chloro-3-methylbenzoyl)-N'-tert-butylhydrazine,
N-(3-methoxy-2-methylbenzoyl)-N'-(4-chloro-2-methoxybenzoyl)-N'-tert-butylhydrazine,
N-(3-methoxy-2-methylbenzoyl)-N'-(3-bromo-5-methylbenzoyl)-N'-tert-butylhydrazine,
N-(3-methoxy-2-methylbenzoyl)-N'-(4-chlorobenzoyl)-N'-tert-butylhydrazine,
N-(3-methoxy-2-methylbenzoyl)-N'-(3-bromo-5-chlorobenzoyl)-N'-tert-butylhydrazine,
N-(3-methoxy-2-methylbenzoyl)-N'-(3,5-difluorobenzoyl)-N'-tert-butylhydrazine,
N-(3-methoxy-2-methylbenzoyl)-N'-(4-methylbenzoyl)-N'-tert-butylhydrazine,
N-(3-methoxy-2-methylbenzoyl)-N'-(3-chloro-4-fluorobenzoyl)-N'-tert-butylhydrazine,
N-(3-methoxy-2-methylbenzoyl)-N'-(3-fluorobenzoyl)-N'-tert-butylhydrazine,
N-(3-methoxy-2-methylbenzoyl)-N'-(3,4-difluorobenzoyl)-N'-tert-butylhydrazine,
N-(3-methoxy-2-methylbenzoyl)-N'-(2-methoxy-4-methylbenzoyl)-N'-tert-butylhydrazine,
N-(3-methoxy-2-methylbenzoyl)-N'-(2,4-dichlorobenzoyl)-N'-tert-butylhydrazine,
N-(3-ethoxy-2-methylbenzoyl)-N'-(3,5-dimethylbenzoyl)-N'-tert-butylhydrazine,
N-(3-methoxy-2-methylbenzoyl)-N'-(3-chlorobenzoyl)-N'-tert-butylhydrazine,
N-(3-methoxy-2-methylbenzoyl)-N'-(3,5-dimethylbenzoyl)-N'neopentylhydrazine,
N-(2-bromo-3-methoxybenzoyl)-N'-(3,5-dimethylbenzoyl)-N'-tert-butylhydrazine,
N-(2-chloro-3-methoxybenzoyl)-N'-(3,5-dimethylbenzoyl)-N'-tert-butylhydrazine,
N-(2-methyl-3-trifluoromethoxybenzoyl)-N'-(3,5-dimethylbenzoyl)-N'-tert-butylhydrazine,
N-(3-methoxy-2-methylbenzoyl)-N'-(4-methylbenzoyl)-N'-tert-butylhydrazine,
N-(3-methoxy-2-methylbenzoyl)-N'-(3-bromo-4-fluorobenzoyl)-N'-tert-butylhydrazine,
N-(3-methoxy-2-methylbenzoyl)-N'-(3-fluoro-4-methylbenzoyl)-N'-tert-butylhydrazine,
N-(3-methoxy-2-methylbenzoyl)-N'-(3-chloro-4-methylbenzoyl)-N'-tert-butylhydrazine,
N-(3-methoxy-2-methylbenzoyl)-N'-(3-chloro-4-methoxybenzoyl)-N'-tert-butylhydrazine,
N-(3-methoxy-2-methylbenzoyl)-N'-(3,4,5-trichlorobenzoyl)-N'-tert-butylhydrazine,
N-(3-methoxy-2-methylbenzoyl)-N'-(3-ethylbenzoyl)-N'-tert-butylhydrazine,
N-(3-methoxy-2-methylbenzoyl)-N'-(3,5-dichloro-4-fluorobenzoyl)-N'-tert-butylhydrazine,
N-(2-ethyl-3-methoxybenzoyl)-N'-(3,5-dimethylbenzoyl)-N'-tert-butylhydrazine,
N-(2-ethyl-3-methoxybenzoyl)-N'-(3-chloro-5-methylbenzoyl)-N'-tert-butylhydrazine,
N-(2-ethyl-3-methoxybenzoyl)-N'-(3,5-difluorobenzoyl)-N'-tert-butylhydrazine,
N-(2-ethyl-3-methoxybenzoyl)-N'-(3-methoxybenzoyl)-N'-tert-butylhydrazine,
N-(2-ethyl-3-methoxybenzoyl)-N'-(3-methylbenzoyl)-N'-tert-butylhydrazine,
N-(2-ethyl-3-methoxybenzoyl)-N'-(3,5-dichlorobenzoyl)-N'-tert-butylhydrazine,
N-(2-ethyl-3-methoxybenzoyl)-N'-(2,4-dichlorobenzoyl)-N'-tert-butylhydrazine,
N-(2-ethyl-3-methoxybenzoyl)-N'-(2-chloro-5-methylbenzoyl)-N'-tert-butylhydrazine,
N-(2-chloro-3-methoxybenzoyl)-N'-(3,5-dimethylbenzoyl)-N'-tert-butylhydrazine,
N-(2-bromo-3-methoxybenzoyl)-N'-(3,5-dimethylbenzoyl)-N'-tert-butylhydrazine,
N-(2-methyl-3,4-methylenedioxybenzoyl)-N'-(3,5-dimethylbenzoyl)-N'-tert-butylhydrazine,
N-(2-ethyl-3,4-methylenedioxybenzoyl)-N'-(3,5-dimethylbenzoyl)-N'-tert-butylhydrazine,
N-(2-chloro-3,4-methylenedioxybenzoyl)-N'-(3,5-dimethylbenzoyl)-N'-tert-butylhydrazine,
N-(2-bromo-3,4-methylenedioxybenzoyl)-N'-(3,5-dimethylbenzoyl)-N'-tert-butylhydrazine,
N-(3,4-(1,2-ethylenedioxy)-2-methylbenzoyl)-N'-(3,5-dimethylbenzoyl)-N'-tert-butylhydrazine, and
N-(2-ethyl-3,4-(1,2-ethylenedioxy)benzoyl)-N'-(3,5-dimethylbenzoyl)-N'-tert-butylhydrazine.

Even more preferred compounds and compositions thereof because of their outstanding insecticidal activity against insects of the order Lepidoptera include:

N-(3-methoxy-2-methylbenzoyl)-N'-(3-chloro-5-methylbenzoyl)-N'-tert-butylhydrazine,
N-(3-methoxy-2-methylbenzoyl)-N'-(3,5-dimethylbenzoyl)-N'-tert-butylhydrazine, N-(3-methoxy-2-methylbenzoyl)-N'-(3-methylbenzoyl)-N'-tert-butylhydrazine,
N-(3-methoxy-2-methylbenzoyl)-N'-(3,5-dichlorobenzoyl)-N'-tert-butylhydrazine,
N-(3-methoxy-2-methylbenzoyl)-N'-(3,4-dichlorobenzoyl)-N'-tert-butylhydrazine,
N-(3-ethoxy-2-methylbenzoyl)-N'-(3,5-dimethylbenzoyl)-N'-tert-butylhydrazine,
N-(3-methoxy-2-methylbenzoyl)-N'-(3-methoxy-5-methylbenzoyl)-N'-tert-butylhydrazine,
N-(3-methoxy-2-methylbenzoyl)-N'-(4-fluorobenzoyl)-N'-tert-butylhydrazine,
N-(2-chloro-3-methoxybenzoyl)-N'-(3,5-dimethylbenzoyl)-N'-tert-butylhydrazine,
N-(2-bromo-3-methoxybenzoyl)-N'-(3,5-dimethylbenzoyl)-N'-tert-butylhydrazine,
N-(3,4-(1,2-ethylenedioxy)-2-methylbenzoyl)-N'-(3,5-dimethylbenzoyl)-N'-tert-butylhydrazine, and
N-(2-ethyl-3,4-(1,2-ethylenedioxy)benzoyl)-N'-(3,5-dimethylbenzoyl)-N'-tert-butylhydrazine.

More preferred compounds and compositions thereof because of their superior insecticidal activity against insects of the order Homoptera include:
N-(2-ethyl-3-methoxybenzoyl)-N'-(3,5-dimethylbenzoyl)-N'-tert-butylhydrazine,
N-(2-ethyl-3-methoxybenzoyl)-N'-(3-chloro-5-methylbenzoyl)-N'-tert-butylhydrazine,
N-(2-ethyl-3-methoxybenzoyl)-N'-(3-methoxybenzoyl)-N'-tert-butylhydrazine,
N-(2-ethyl-3-methoxybenzoyl)-N'-(2-methoxybenzoyl)-N'-tert-butylhydrazine,
N-(2-ethyl-3-methoxybenzoyl)-N'-(2-chlorobenzoyl)-N'-tert-butylhydrazine,
N-(3-ethoxy-2-ethylbenzoyl)-N'-(3,5-dimethylbenzoyl)-N'-tert-butylhydrazine,
N-(2-ethyl-3-methoxybenzoyl)-N'-(3-methylbenzoyl)-N'-tert-butylhydrazine,
N-(3,4-(1,2-ethylenedioxy)-2-methylbenzoyl)-N'-(3,5-dimethylbenzoyl)-N'-tert-butylhydrazine, and
N-(2-ethyl-3,4-(1,2-ethylenedioxy) benzoyl)-N'-(3,5-dimethylbenzoyl)-N'-tert-butylhydrazine.

Methods of Preparation

Many of the compounds of the present invention, and the intermediates related thereto, can be prepared by methods similar to the known methods for making N'-substituted-N,N'-diacylhydrazines. Those of ordinary skill in the art will be able to utilize or modify such processes after knowledge of the disclosures herein to accommodate many of the functionalities $R^c$, $R^d$, $R^e$ and $R^f$ in the intermediates and compounds of the present invention.

An inventive method to produce some of the intermediates desirable to produce the $R^a$ and $R^b$ functionalities of the present invention has been discovered. This method provides unexpected results in the products and safety of the reaction involved as well as provides a simplified, economic process. The method can be performed by a process comprising effectively admixing a 3-amino-2-(substituted)benzoic acid, sodium nitrite and an alcohol, preferably methanol or ethanol, or a mixture of water and an alcohol, preferably only an alcohol, under acidic conditions to produce a reaction mass comprising a 3-alkoxy-2-(substituted)benzoic acid, preferably 3-methoxy-2-(substituted)benzoic acid or 3-ethoxy-2-(substituted)benzoic acid.

Accordingly, one process embodiment of the present invention is a process comprising admixing (a) a composition comprising
  (i) a 3-amino-2-(substituted)benzoic acid or an ester thereof and
  (ii) an alcohol or a mixture of an alcohol and water, preferably methanol or ethanol;
(b) an effective amount of an inorganic acid; and
(c) sodium nitrite.

The general reaction scheme can be depicted as follows:

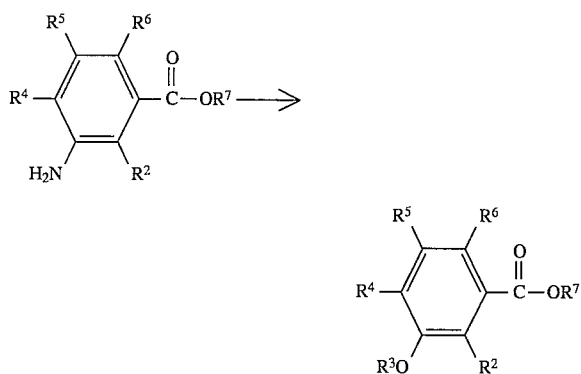

Each of $R^2$, $R^4$, $R^5$, and $R^6$ independently can be hydrogen, a straight or branched $(C_1-C_{10})$alkyl, a straight or branched halo$(C_1-C_{10})$alkyl, a straight or branched $(C_1-C_{10})$alkoxy, a straight or branched halo$(C_1-C_{10})$alkoxy, or a halo substituent. Preferably $R^2$ is a substituent consistent with the desired compound substitution. Preferred 3-amino-2-(substituted)benzoic acids are 3-amino-2-methylbenzoic acid and 3-amino-2-ethylbenzoic acid. Preferred halo substituents are are bromo, chloro, and fluoro. A preferred halo$(C_1-C_{10})$alkyl is trifluoromethyl. $R^3$ is an alkyl moiety, preferably lower alkyl and more preferably methyl or ethyl, which results from the use of an alcohol in the process having the formula $R^3OH$.

$R^7$ can be hydrogen, a straight or branched $(C_1-C_{10})$alkyl, or a straight or branched halo$(C_1-C_{10})$alkyl. Non-limiting illustration of a straight or branched $(C_1-C_{10})$alkyl can be n-butyl as a straight $C_4$ alkyl and sec-butyl or isobutyl as a branched $C_4$ alkyl. The halogenated alkyls can be halogenated with one or more of the same or different halogen. Preferably, $R^7$ is a hydrogen or a $(C_1-C_4)$alkyl, more preferably hydrogen. Some replacement of $R^7$ on the product compound can occur, thus creating a product mixture of acids and esters.

The acidic condition can be created by use of hydrobromic, hydrochloric, phosphoric, or sulfuric acid; preferably sulfuric acid. The amount of the acid is that effective amount in combination with the utilized water or methanol to produce the desired alkoxylated product in substantial amounts. The amount of acid can range from about 0.5 to about 5 mole equivalents, preferably from about 1 to about 4 mole equivalents, more preferably from about 1.5 to about 2.5 mole equivalents.

The amount of alkoxylated product produced in the reaction mass is preferably at least about sixty (60) per cent by weight, more preferably at least about eighty (80) per cent.

The reaction mass can comprise additional products consisting of hydroxylated products (e.g., "phenolic compounds") which have hydroxyl (OH) moieties at the 3 position (e.g., 3-hydroxy-2-methylbenzoic acid). Preferably, the hydroxylated by-product content of the reaction mass is less than ten (10) per cent by weight, more preferably less than about five (5) per cent by weight, and most preferably essentially an absence of the hydroxylated by-product.

The reaction mass also can comprise additional products which have replacement moieties bonded to the "oxy" oxygen of the carboxylic group of the 3-aminobenzoic acid [e.g., —$CO_2H$→—$CO_2R^3$], wherein $R^3$ can be the alkyl portion of the alcohol used, e.g. methyl.

The reaction temperature can be room temperature up to the boiling temperature of the reaction mixture, although cooling can be done but is not required. Preferably the temperature is from about 0° C. to about 100° C., more preferably from about 25° C. to about 75° C., most preferably from about 45° C. to about 65° C.

Since some phenolic by-product may be produced by the reaction, an optional method of additional steps to convert any phenolic by-product produced in the reaction comprises subsequently admixing the reaction mass formed containing such phenolic compounds with (a) art effective amount of a base, preferably sodium hydroxide, potassium hydroxide, sodium carbonate, or potassium carbonate, more preferably sodium hydroxide and potassium hydroxide, and (b) an effective amount of a methylating agent, preferably methyl carbonate, methyl chloride, methyl iodide or dimethyl sulfate, to convert a substantial amount, preferably essentially all, of the phenol compounds to a 3-methoxybenzoic acid or 3-methoxybenzoic ester derivative compound.

The amount of the base used can be preferably about 4 to about 6 equivalents and the amount of the methylating agent used can be preferably about 2 to about 4 equivalents.

Such processes result unexpectedly in a more safe and direct one step route to production of the 3-methoxybenzoic acid relative to prior known processes, which exhibit potential explosion hazards. The enhanced safety is due in part to avoidance of the build-up of diazonium intermediates during the course of the reaction.

Another inventive method to produce some of the intermediates desirable to produce the $R^a$ functionality in the presence of certain heterocyclic rings fused to the $R^b$ and $R^h$ position has been discovered. This method provides unexpected results in the products and ease of the reaction involved as well as providing a simplified economic process. The method can be performed by a process comprising effectively of mixing a 3,4-fused heterocyclic benzoic acid with an alkyl lithium reagent at low temperature, followed by addition of an electrophilic reagent to produce a reaction mass containing a 2-substituted-3,4-fused heterocyclic benzoic acid. Thus, this method permits direct ortho-lithiation of certain benzoic acid derivatives in the presence of a carboxy group and obviates the need for other activating/protecting groups in place of the carboxy group.

Accordingly, a second process embodiment of the present invention is a process comprising admixing at a temperature of from about −90° C. to about −20° C. for from about one to about four hours (a) a composition comprising
    (i) a 3,4-fused heterocyclic benzoic acid and
    (ii) an aprotic solvent, and
(b) a composition comprising
    (i) an alkyl lithium reagent and
    (ii) an aprotic solvent, followed by subsequent admixture of
(c) an electrophilic reagent at from about −90° C. to about room temperature.

The general reaction scheme can be depicted as follows:

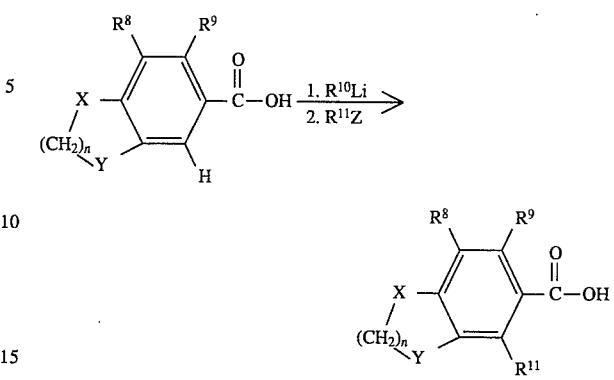

Each of $R^8$ and $R^9$ independently may be hydrogen, a straight or branched ($C_1$–$C^{10}$)alkyl, or a or straight or branched ($C_1$–$C_{10}$)alkoxy. Preferably, $R^8$ and $R^9$ are hydrogen. X may be methylene ($CH_2$), oxy (O), thio (S) or N—$R^{12}$, where $R^{12}$ may be a straight or branched ($C_1$–$C_{10}$)alkyl. Y may be oxy, thio or N when N forms a double bond with an adjacent carbon atom. Preferably, X is O or $CH_2$ and Y is O. The methylene chain length represented by n may be 1–3, preferably 1 or 2.

The lithiating reagent $R^{10}$Li may be n-butyl lithium, sec-butyl lithium, tert-butyl lithium, or phenyl lithium, preferably n-butyl lithium.

The aprotic reaction solvent may be tetrahydrofuran, ethyl ether, 1,4-dioxane, hexanes, or mixtures of these. The preferred solvent is tetrahydrofuran.

The reaction mixture may also contain adjunctive lithium chelators such as tetramethylethylenediamine (TMEDA).

The electrophilic reagent is represented by the formula $R^{11}Z$ wherein $R^{11}$ is lower alkyl, preferably methyl or ethyl, perhaloalkyl, or is a halo such as chloro, bromo or iodo, and Z is a halo such as chloro, bromo or iodo, an alkylcarbonyl such as acetyl or propionyl, an alkylcarbonyloxy such as acetoxy, or formyl. More preferably, the electrophile is a lower alkyl iodide, such as methyl or ethyl iodide.

The reaction temperature for ortho-lithiation can be from about −90° to about −20° C., preferably from about −50° to about −80° C.

The reaction time for ortho-lithiation may be about 1–4 hours, preferably about 2 hours.

The reaction temperature for reaction of the electrophilic reagent can be from about −90° C. to about room temperature. Preferably, the electrophilic reagent is added at about −65° C. and the reaction mixture is permitted to warm to about room temperature without additional heating.

The reaction time for reaction of the electrophilic reagent can be from about 30 minutes to about 2 hours.

Such processes unexpectedly result in a simple one-step route to 2-substituted benzoic acids which also bear a fused heterocycle at the 3 and 4 positions. This process minimizes the reaction of the alkyl lithium reagent with the carbonyl group resulting in undesired phenyl ketones, and obviates the need for other activating/protecting groups in place of the carboxy group.

The agronomically acceptable salts of the present insecticidal compounds can be synthesized by the utilization of the salting methods known in the art relating to N'-substituted-N,N'-diacylhydrazines used as insecticides.

The compounds of the present invention exhibit unexpectedly excellent results in their use as insecticides. One skilled in the art will be able to determine the activity of a given compound against a given insect and the dosage required to obtain unexpectedly good insecticidal effects. The exact dosage for a given situation can be routinely determined and the compositions and formulations for such uses, and the desired additional components (such as agronomically acceptable carriers, diluents, extenders and other common additives used in insecticidal compositions) can be determined in the known manners.

Accordingly, another embodiment is an insecticidal composition comprising one or more compounds having the formula N-(2-$R^a$-3-$R^b$-4-$R^h$-benzoyl)-N'-(2-$R^c$-3-$R^d$-4-$R^e$-5-$R^f$-benzoyl)-N'-$R^g$-hydrazine wherein $R^a$ is a halo or lower alkyl; $R^b$ is lower alkoxy, optionally substituted with halo (preferably fluoro); $R^c$ is selected from hydrogen, bromo, chloro, fluoro, lower alkyl, lower alkoxy, lower alkoxy lower akyl, and nitro; $R^d$, $R^e$ and $R^f$ are each independently selected from hydrogen, bromo, chloro, fluoro, lower alkyl, lower alkoxy, and lower alkoxy lower alkyl; $R^g$ is a ($C_4$-$C_6$)alkyl; $R^h$ is hydrogen, lower alkoxy, lower alkyl, or when taken together with $R^b$ is methylenedioxy (—OCH$_2$O—), 1,2-ethylenedioxy (—OCH$_2$CH$_2$O—), 1,2-ethyleneoxy (—CH$_2$CH$_2$O—) or 1,3-propyleneoxy (—CH$_2$CH$_2$CH$_2$O—) wherein an oxo atom is located at the $R^b$ position; and the substituents $R^c$ and $R^d$, or $R^d$ and $R^e$, or $R^e$ and $R^f$ when taken together can be methylenedioxy or 1,2-ethylenedioxy. The preferred compositions have the preferred compounds set out hereinabove.

Also embodied is a method for controlling insects comprising contacting the insect with an insecticidally effective amount of a compound having the formula N-(2-$R^a$-3-$R^b$-4-$R^h$-benzoyl)-N'-(2-$R^c$- 3-$R^d$-4-$R^e$-5-$R^f$-benzoyl)-N'-$R^g$-hydrazine wherein $R^a$ is a halo or lower alkyl; $R^b$ is lower alkoxy, optionally substituted with halo (preferably fluoro); $R^c$ is selected from hydrogen, bromo, chloro, fluoro, lower alkyl, lower alkoxy, lower alkoxy lower alkyl, and nitro; $R^d$, $R^e$ and $R^f$ are each independently selected from hydrogen, bromo, chloro, fluoro, lower alkyl, lower alkoxy, and lower alkoxy lower alkyl; $R^g$ is a ($C_4$-$C_6$)alkyl; $R^h$ is hydrogen, lower alkoxy, lower alkyl, or when taken together with $R^b$ is methylenedioxy (—OCH$_2$O—), 1,2-ethylenedioxy (—OCH$_2$CH$_2$O—), 1,2-ethyleneoxy (—CH$_2$CH$_2$O—) or 1,3-propyleneoxy (—CH$_2$CH$_2$CH$_2$O—) wherein an oxo atom is located at the $R^b$ position; and the substituents $R^c$ and $R^d$, or $R^d$ and $R^e$, or $R^e$ and $R^f$ when taken together can be methylenedioxy or 1,2-ethylenedioxy. The preferred methods will utilize the preferred compounds hereinabove identified. A preferred method is a method wherein $R^a$ is methyl, ethyl, chloro or bromo, $R^b$ is methoxy and $R^h$ is hydrogen or when $R^b$ and $R^h$ taken together are methylenedioxy or 1,2-ethylenedioxy, $R^g$ is tert-butyl, and wherein no more than three of $R^c$, $R^d$, $R^e$ and $R^f$ are the same member selected from a group consisting of bromo, fluoro and chloro or no more than two of $R^d$, $R^e$ and $R^f$ are methoxy.

The following examples illustrate preparation of the 3-alkoxy-2-alkylbenzoic acids, the 3,4-fused heterocyclic benzoic acids, intermediates, and representative compounds of the present invention.

EXAMPLE 1

Preparation of 3-Methoxy-2-Methylbenzoic Acid

3-Amino-2-methylbenzoic acid, 140.3 grams (g), 0.93 mole, reacted in four portions) in 5.7 mass equivalents of methanol, was treated with 1.5 mole equivalents of concentrated sulfuric acid. The mixture was heated to 55° C. and 1.05 mole equivalent of sodium nitrite dissolved in twice its mass of water was fed to the reaction over 30 to 45 minutes, maintaining the temperature between 55° and 65° C. Then 4.5 mole equivalents of 25% aqueous sodium hydroxide was added over one-half hour, followed by a half-hour feed of 2 mole equivalents of dimethyl sulfate at 50° to 60° C. After one-half hour the batch was assayed by gas chromatography (GC). Additional sodium hydroxide and dimethyl sulfate were added in portions until complete conversion was obtained, The methanol remaining was removed by vacuum, and the residue was partitioned between ethyl acetate and water made acidic with sulfuric acid. The ethyl acetate was removed under vacuum. The combined residues (152.8 g) dissolved in 350 g warm methanol were poured into a mixture of 278 g concentrated sulfuric acid and 1 liter (L) water. The resulting precipitate was collected by filtration, washed with water, and dried in vacuo, giving 135.8 g of material which was 96% pure as determined by GC.

EXAMPLE 2

Preparation of 3-Chloro-5-Methylbenzoic Acid

A mixture containing 3,5-dimethylchlorobenzene (25 g, 180 mmoles), cobalt (II) acetate tetrahydrate (1.1 g, 4.5 mmol), and sodium bromide (0.46 g, 4.5 mmoles) in 50 milliliters (mL) of acetic acid was heated to 85° C. while air was bubbled in. After 55 h, the reaction was judged to be complete by GC. After cooling to room temperature, the reaction mixture was filtered. The filtrate was partitioned between water (500 mL) and ethyl acetate (200 mL). The aqueous was extracted with 2×100 mL ethyl acetate. The combined organic phases were washed with water, then extracted with 4% aqueous sodium hydroxide (3×200 mL). The basic aqueous phases were cooled with ice and acidified with concentrated hydrochloric acid. The resulting white precipitate was collected by vacuum filtration and dried to yield 15.5 g of white solid (mp 175°–177° C.) which was consistent with the structure 3-chloro-5-methyl benzoic acid by nmr and GC.

EXAMPLE 3

Preparation of 3-Amino-2-Methylbenzoic Acid

A solution of 2-methyl-3-nitrobenzoic acid (mp. 182°–184° C., 22 g, 0.12 mol) in 400 mL of methanol was hydrogenated over platinum oxide (100 mg) for 45 minutes at 55 pounds per square inch (psi), whereupon the catalyst was filtered off through a bed of Celite® (50 g), and the solvent evaporated under reduced pressure to give 3-amino-2-methylbenzoic acid (mp. 178°–181° C.) in quantitative yield (18.3 g).

EXAMPLE 4

Preparation of 3-Methoxy-2-Methylbenzoic Acid

Ground 3-amino-2-methylbenzoic acid (17 g, 0.11 mole) was mixed with methanol (120 mL) in a 1-13-neck round bottom flask provided with a mechanical stirrer and a thermometer. To this mixture, concentrated sulfuric acid, 15.5 mL, was added dropwise with stirring. Upon the addition, the temperature of the mixture went up to 50° C. The addition time was 2 minutes. Following the addition, the flask was placed on a pre-heated oil bath and the temperature of 50°–55° C. inside the flask was maintained. Thereafter, a dropwise addition of sodium nitrite solution (8.1 g in 17 mL of water) was started. When the temperature reached 62° C., the heating under the oil bath was turned off. After additional 10 min on the oil bath (the heater still turned off), the temperature dropped to 55° C., at which point sodium hydroxide (50% aqueous, 55 g) diluted water (55 mL) was added dropwise over 30 minutes, followed by water (55 mL) in one portion, and dimethyl sulfate (25 mL) dropwise in two portions (15 mL plus 10 mL) over 30 minutes with 20 minutes apart. The reaction mixture was allowed to cool to room temperature whereupon it was poured over concentrated sulfuric acid, 40 mL, diluted with water (360 mL), the product collected by filtration, and dried in vacuo over 24 hours to give 3-methoxy-2-methylbenzoic acid (12 g). $^1$H-NMR (CDCl$_3$) δppm 2.50 (s, 3H), 3.85 (s, 3H), 7.03 (d 1H, Ar), 7.22 (dd, 1H, C-5), 7.59 (d, 1H, Ar).

EXAMPLE 5

Preparation of 3-Methoxy-2-Methylbenzoyl Chloride

To 3-methoxy-2-methylbenzoic acid (454 g, 2.73 moles) in 1300 mL chloroform containing 20 g dimethyl formamide at 65° C., thionyl chloride (390 g) was added dropwise over 6 hours, whereupon the solvent was removed by evaporation at a reduced pressure. The residue (512 g) was distilled at 110° C. at 1–2 mm Hg to give 3-methoxy-2-methylbenzoyl chloride (435 g).

EXAMPLE 6

Preparation of N-(3,5-Dimethylbenzoyl)-N-tert-Butyl-Hydrazine

A suspension of tert-butylhydrazine (290 g, 2.33 moles) in toluene (830 mL) was cooled to 5° C. in an ice bath. Sodium hydroxide (50% aqueous; 180 g, 2.25 moles) mixed with ice (180 g) was slowly added over 30 minutes. To this was added di-tertbutyl dicarbonate (500 g; 2.29 moles) over 2 hours, while the temperature of the reaction kept close to 5° C. After the completion, the reaction was allowed to warm to room temperature and stirred overnight. The organic layer was then washed with water and brine, dried over magnesium sulfate, filtered and stripped. The crude product was recrystallized from hexane to give a solid (338.7 g) which melted at 83°–86° C. To this solid (320 g, 1.69 mol) in toluene (1 L) at 7° C., 3,5-dimethylbenzoyl chloride (268 g, 1.59 moles) and sodium hydroxide (50% aqueous, 127.23g, 1.59 moles) were added concurrently at such a rate that the temperature of the reaction mixture remained 5°–9° C. After addition was complete (2 hours), the reaction mixture was allowed to reach room temperature, whereupon it was diluted with hexane and water, and the product filtered. Additional product was obtained by washing the organic portion of the filtrate with water and brine, evaporation of the solvent followed by trituration with hexane. The combined filtercake (470 g, 1.5 moles) was suspended in methanol (1500 mL) and treated with 37% hydrochloric acid (357 mL, 3.62 moles) at such a rate that the temperature remained below 35° C. Cooling on ice bath was applied. After the addition was complete, the reaction mixture was stirred for 72 hours. Additional hydrochloric acid (50 mL) was added and reaction stirred briefly, then neutralized with aqueous sodium bicarbonate. The product was filtered, washed with water and dried to give 256 g of N-(3,5-dimethylbenzoyl)-N-tert-butylhydrazine. $^1$H-NMR δppm 1.47 (s, 9H, t-Bu) 2.31 (s, 6H), 3.73 (s broad, 2H, NH$_2$) 7,00 (s, 1H, C-4), 7,05 (s, 2H, Ar- C-2 and 6).

EXAMPLE 7

Preparation of N-(3-methoxy-2-methylbenzoyl)-N'-(3,5-dimethylbenzoyl)-N'-tert-butylhydrazine from Products of EXAMPLES 4 and 6

A solution of 3-methoxy-2-methylbenzoic acid (1.5 g, 0.01 mole) in thionyl chloride (10 mL.) was refluxed for 45 minutes and then stripped under reduced pressure. The residue was dissolved in methylene chloride (50 mL) and added dropwise with cooling at 0° C. to a solution of N-(3,5-dimethylbenzoyl)-N-tert-butylhydrazine (4.4 g. 0.02 mole) in methylene chloride (50 mL). Following the addition, the solution was stirred overnight at room temperature and filtered. The filter-cake was washed extensively with water and ether, and then dried in vacuo to give 2.1 g of N-(3-methoxy-2-methylbenzoyl)-N'-(3,5-dimethylbenzoyl)-N'-tert-butylhydrazine, melting at 204°–204.5° C. $^1$H-NMR δppm 1.50 (s, 9H, tert-Bu), 1.63 (s, 3H, Ar—CH$_3$), 2.25 (s, 6H, di—CH$_3$) 3.75 (s, 3H, OCH$_3$), 6.26 (d, 1 H, Ar), 6.93–7.20 (m, 5H, Ar).

EXAMPLE 8

Preparation of N-(3-Methoxy-2-Methylbenzoyl)-N'-tert-Butylhydrazine from Product of EXAMPLE 5

To a stirred suspension of tert-butylhydrazine hydrochloride (397 g, 3.27 mole) in methylene chloride (2 L) at 0° C., was added sodium hydroxide (50% aqueous, 260 g) diluted with water (400 mL). Following this, 3-methoxy-2-methylbenzoyl chloride (140 g, 0.78 mole) in methylene chloride (1 L) and sodium hydroxide (50% aqueous, 80 g) dilutect with water (400 mL) were added concurrently at −20° C. After the addition was complete, the reaction mixture was allowed to warm to room temperature and after additional 30 minutes, the organic layer was washed with water (4×500 mL), dried over magnesium sulfate and stripped to yield N-(3-methoxy-2-methylbenzoyl)-N'-tert-butylhydrazine (177 g). $^1$H-NMR (CDCl$_3$) δppm 1.19 (s, 9H, t-Bu), 2.29 (s, 3H, CH$_3$), 3.87 (s, 3H, OCH$_3$), 6.90 (d, 1H, C-4 or 6), 6.95 (d, 1H, C-4 or C6) 7.19 (dd, 1H, C-5).

EXAMPLE 9

Preparation of N-(3-Methoxy-2-Methylbenzoyl)-N'-(3,5-Dimethylbenzoyl)-N'-tert-Butylhydrazine from Product of EXAMPLE 8

To a stirred solution of N-(3-methoxy-2-methylbenzoyl)-N'-tert-butylhydrazine (506 g, 2.14 mole) in methylene chloride (1.5 L) at 5° C. were simultaneously added solutions of 3,5-dimethylbenzoyl chloride (360 g, 2.14 moles) in methylene chloride (500 mL) and sodium hydroxide (50% aqueous, 171.2 g, 2.14 moles) diluted with water (400 mL), at such a rate that the temperature of the mixture did not exceed 10° C. Following the addition, the reaction mixture was allowed to reach room temperature and stirred continuously for 1 additional hour, whereupon the reaction mixture was diluted with methylene chloride (12 L), washed with water, dried over magnesium sulfate, filtered and stripped to give N-(3-methoxy-2-methylbenzoyl)-N'-(3,5-dimethylbenzoyl)-N'-tert-butylhydrazine (663 g), melting at 204°–204.5° C.

EXAMPLE 10

Preparation of 2-(3-Methoxyphenyl)-5,5-Dimethyloxazoline

To a 500 mL, 3-neck, round-bottom flask equipped with thermometer, condenser, addition funnel, and magnetic stirring, was added 43.2 g (253 mmoles) of m-anisoyl chloride in 500 mL of methylene chloride. The solution was cooled on ice and 2-methyl-2-aminopropanol (56.4 g, 60.4 mL, 633 mmoles) dissolved in 50 mL of methylene chloride was added slowly with stirring. The mixture was allowed to warm to room temperature and was stirred overnight. The solution was filtered from solids, and solvent was removed in vacuo. With ice cooling, thionyl chloride (90.8 g, 55.7 mL, 763 mmoles) was added to the remaining oil. The mixture was stirred for 1 hour at room temperature, and poured into 1 L of ether. The ether was decanted, and the remaining oil was carefully poured into 100 mL of 20% sodium hydroxide with ice cooling. After extraction several times with ether, the organic phases were combined, dried over magnesium sulfate, and solvent was removed in vacuo to yield a viscous yellow oil. The crude material was purified by column chromatography (1:1 ether:hexanes), or by distillation (5 mm Hg, b.p.=150° C.), to yield a low-melting solid.

EXAMPLE 11

Preparation of 2-Ethyl-3-Methoxybenzoic Acid

A 5 L, 4-necked round-bottom flask equipped with addition funnel, overhead stirring, and nitrogen purge was dried and charged with 128 g (623 mmoles) of 2-(3-methoxyphenyl)-5,5-dimethyloxazoline in 2.5 L of tetrahydrofuran. The mixture was cooled to −65° C. in a dry ice/isopropanol bath, and 450 mL of 1.6N n-butyl lithium was added slowly. After complete addition, the mixture was stirred for 1.5 hours at −45° to −30° C. After cooling to −45° C., ethyl iodide was added (80 mL, 1 mole). The temperature was maintained at −45° C. for 20 minutes, the mixture was allowed to warm to room temperature and was stirred overnight. Saturated ammonium chloride was added with ice cooling, and the mixture extracted several times with ether. The organic extracts were combined, dried over sodium sulfate, and solvent was removed in vacuo to give an oily solid. The solid was dissolved in 1 L of 6N hydrochloric acid in 3:1 water:methanol and heated at reflux for 15 hours. The hydrolysis was monitored by $^1$H NMR and shown to be about 75% complete. Additional acid was added (200 mL of 6N hydrochloric acid in 3:1 water:methanol), and the mixture was heated again at reflux for 8 hours. The mixture was cooled on ice, solids were collected, and dissolved in 10% aq. sodium hydroxide/methylene chloride. The aqueous layer was removed, acidified, and filtered to yield a tan solid which was air-dried at room temperature (53 g). An additional 23 g of product was obtained by further acidic hydrolysis of the methylene chloride extract. The melting point of the desired acid was 100°–101° C.

EXAMPLE 12

Preparation of N-(2-Ethyl-3-Methoxybenzoyl)-N'-(3,5-Dimethylbenzoyl)-N'-tert-Butylhydrazine To a 25 mL round-bottom flask was added 2-ethyl-3-methoxybenzoyl chloride (0.52 g, 2.9 mmoles) and 2 mL thionyl chloride. The mixture was heated at reflux for two hours, and excess thionyl chloride was removed in vacuo to yield 2-ethyl-3-methoxybenzoyl chloride as a tan solid.

The acid chloride and 0.60 g (2.72 mmoles) N-t-butyl-N-3,5-dimethylbenzoylhydrazine was dissolved in 5 mL of methylene chloride and the solution was cooled in an ice bath. Potassium carbonate (0.83 g, 6.0 mmoles) in 2 mL of water was added and the mixture was stirred gently first at 0° C. for several hours, and then at room temperature overnight. The methylene chloride layer was removed, and the mixture was extracted once again with methylene chloride. The organic phases were combined, dried over magnesium sulfate, and the solvent was evaporated. The resultant solid was washed several times with 1:1 ether:hexanes and dried for one hour at 70° C. to yield 1.0 g, m.p. 146° C.

EXAMPLE 13

Preparation of 2-Ethyl-3-Methoxy-4-Methylbenzoic Acid 2-(2-Ethyl-3-methoxy-4-methylphenyl)-5,5-dimethyloxazoline, synthesized in like manner according to EXAMPLE 10, (2.7 g, 13.1 mmoles) and 2.2 mL (35.3 mmoles) of methyl iodide were dissolved in 4 mL of dimethyl sulfoxide. The resultant mixture was stirred for 18 hours at room temperature. A solution of 4.2 g of potassium hydroxide in 35 mL of water was added, and the mixture was heated at reflux for 8 hours. About 40 g ice was added, and the solution was extracted with ether. The aqueous layer was cooled on ice and acidified with 5% hydrochloric acid. The resulting precipitate was filtered and air-dried to yield 1.69 g of product. $^1$H NMR (200 MHz, CDCl$_3$), δ=7.72 (1H, d, 8 Hz), 7.1 (1H, d, 8 Hz), 3.77 (3H, s), 3.06 (2H, q, 7 Hz), 2.36 (3H, s), 1.22 (3H, t, 7 Hz) ppm.

EXAMPLE 14

Preparation of 2-Methylpiperonylic Acid

A 250 mL round-bottom flask equipped with a nitrogen purge, septum inlet, and magnetic stirring was dried under a nitrogen atmosphere and charged with 2.5 g (15 mmoles) of piperonylic acid and 100 mL of tetrahydrofuran. The solution was cooled to −70° C., and n-butyl lithium (1.6M, 22 mL, 35.2 mmoles) was added. The mixture was stirred for 2 hours at −70° C. Methyl iodide (3 mL, 48.2 mmoles) was added at ≦−65° C., the mixture was stirred for 1 hour at −70° C., and the solution was then allowed to warm to 0° C. The reaction was quenched with saturated aqueous ammonium chloride, and the organic layer was removed and acidified with dilute hydrochloric acid to yield 1.37 g of product. Acidification of the aqueous and organic phases gave a total of 2.67 g of a yellow, powdery solid. $^1$H NMR (200 MHz, DMSO-d$_6$), δ=7.5 (1H, d, 8 Hz), 6.83 (1H, d, 8 Hz), 6.08 (2H, s), 2.37 (3H, s) ppm.

EXAMPLE 15

Preparation of 2-Isopropyl-3-Methoxybenzoic Acid

A 500 mL round-bottom flask equipped with nitrogen purge, septum inlet, and magnetic stirring, was dried under an atmosphere of nitrogen and charged with 5 g (21.2 mmoles) of 2-(2,3-dimethoxyphenyl)-5,5-dimethyloxazoline (which was synthesized in a like manner according to EXAMPLE 10) and 100 mL of tetrahydrofuran. The solution was cooled to 10° C. and 58 mL of 2N isopropylmagnesium chloride/ether was added. The mixture was stirred at room temperature overnight and poured into a 1:1 mixture of saturated ammonium chloride and ice. The mixture was extracted twice with ether; the organic layers were combined, dried over magnesium sulfate, and the solvent was removed in vacuo to yield 5.3 g of a yellow oil. This was dissolved in 200 mL of 6N hydrochloric acid and heated at reflux for 8.5 hours. The mixture was extracted several times with ether, and the combined organic phases were dried over sodium sulfate. The solvent was removed in vacuo to yield 4.6 g of oil which crystallized on standing. $^1$H NMR (200 MHz, CDCl$_3$), δ=7.29 (1H, dd, 1.5, 7.5 Hz), 7.21 (1H, t, 7.5 Hz), 7.01 (1H, dd, 1.5, 7 Hz), 3.85 (3H, s), 3.65 (1H, m), 1.37 (6H, d, 7 Hz) ppm.

EXAMPLE 16

Preparation of 1,4-Benzodioxan-6-carboxylic Acid 1,4-Benzodioxan-6-carboxaldehyde (8.87 g, 54 mmoles), 19.68 g methanol, 50.3 wt % sodium hydroxide (5.99 g) and 30% aqueous hydrogen peroxide (5.30 g, 46.8 mmoles) were heated in a 250 mL flask for 17 minutes at 39°–52° C. and 18 minutes at 52°–58° C. oil bath temperature. After the moderate foaming had subsided, 30% aqueous hydrogen peroxide (13.54 g, 119 mmoles) was added in three roughly equal portions over 22 minutes at 58°–66° C. After a twelve minute hold, two additional portions of 30% hydrogen peroxide (4.24 g and 5.25 g, total now 28.33 g or 250 mmoles) were added 20 minutes apart. Each addition gave moderate transient oxygen evolution. The mixture was heated and stirred for 55 minutes at 67°–47° C. The solution was cooled and 23.62 g of deionized water was added. Neutral oil (2.12 g, predominantly unreacted starting material) was removed by four methylene chloride extractions totaling 10.1 g. Then the extracted aqueous layer was acidified with 37% aqueous hydrochloric acid and the resulting pasty slurry was shaken well. Filtration with three 20 g water washes and drying gave white crystals of 1,4-benzodioxan-6-carboxylic acid (6.97 g), m.p. 134.2°–136.7° C.

EXAMPLE 17

Preparation of 5-Ethyl-1,4-benzodioxan-6-carboxylic Acid

A solution of 1,4-benzodioxan-6-carboxylic acid (6.59 g, 36.6 mmoles) in 96.5 g of dry (0.02% water) tetrahydrofuran was stirred and cooled in a 300 mL flask equipped with a magnetic stirrer, alcohol thermometer and rubber septum stopper connected through a large diameter syringe needle to a nitrogen line. When the mixture had cooled to −71° C. (dry ice/isopropanol bath), 2.5 molar n-butyl lithium in hexanes (16.7 mL) was added over about one minute, giving an exotherm to −28° C. After a 16 minute cooling hold, additional n-butyl lithium solution (total 35 mL) was added in five increments at −70° to −61° C. These additions dissolved most of the fine solid that precipitated when the original solution was cooled. Six minutes later, 16.3 g tetrahydrofuran was added in an attempt to dissolve the remainder of the solid. The suspension was stirred for a total of 4.2 hours at −63° to −72° C. after the final n-butyl lithium addition. Then 99% iodoethane (7.17 g, 46.0 mmoles) was added at −65° C., giving only a slight exotherm. After 19 minutes at about −60° C., the mixture was allowed to warm to 14° C. over 89 minutes and to room temperature over another 16 hours. Then 50.6 g of deionized water was added, a resulting strongly basic aqueous layer (67.4 g) was removed and the organic layer was washed with 15.3 g deionized water/0.85 g 50.3% aqueous sodium hydroxide. The organic layer, containing about 3.1 g of neutral gummy by-products, was discarded. The aqueous layer and wash were acidified and extracted with hexanes/diethyl ether to give crude product containing (by gas chromatography) 61 area % starting acid and 26% of the desired 5-ethyl-1,4-dioxan-6-carboxylic acid.

The crude product in about 14 g of diethyl ether/hexanes was purified by eight stages of partial neutralization/extraction into dilute aqueous sodium hydroxide (the ethylated acid preferentially remained in the organic layers) to give 5-ethyl-1,4-benzodioxan-6-carboxylic acid (0.54 g). The gas chromatographic analysis showed about 88% purity with a melting point of 148°–176° C. The proton NMR spectrum indicated a 92/8 weight ratio of ethylated and unethylated 1,4-benzodioxan-6-carboxylic acid.

Biological Test Methods

In evaluating the insecticidal activity of the compounds of the present invention, the following test procedures were employed.

A test solution containing 600 parts per million (ppm) was made by dissolving a compound of this invention in a 1:1 acetone:methanol solution, then adding water to give a 5:5:90 acetone:methanol:water solution, and finally a surfactant was added at an equivalent of 1 ounce of surfactant per 100 gallons of test solution. Serial dilutions were prepared in water from the 600 ppm solution.

Foliar insecticidal evaluations were made on one or both of the following pests: the Southern Armyworm (SAW), *Spodoptera eridania*, and the Potato Leafhopper (PLH), *Empoasca fabae*.

Whole Plant Tests

For the whole plant Southern Armyworm test, individually potted lima bean plants, *Phaseolus limensis* var. Henderson, were sprayed to runoff (100 gallons per acre) with the test solution using a DeVilbiss Model No. 152 hand sprayer. Upon drying, two leaves were removed from the plant and were placed on moistened filter paper in a Petri dish (100×20 millimeters). The dish was infested with 10 third instar larvae of the Southern Armyworm and covered with the lid. If the larvae were alive three days after treatment, the filter paper was replaced and fresh untreated bean leaves were added. All treatments were maintained at 75°–80° F. under fluorescent light in a well ventilated room. Percent mortality was determined at three and six days after treatment.

For the whole plant Potato Leafhopper test, individually potted fava bean plants, *Vicia faba* var. Long Pod, were sprayed to runoff (100 gallons per acre) with the test solution using a DeVilbiss Model No. 152 hand sprayer. Upon drying, two leaves were removed from the plant and were placed into two Petri dishes (50×9 millimeters), one leaf per dish, on moistened filter pads. Each dish was infested with 5 third instar nymphs of the Potato Leafhopper and covered with the tight fitting lid. All treatments were maintained at 75°–80° F. under fluorescent light in a well ventilated room. Percent mortality was determined at three days after treatment.

Detached Leaf Test

For the detached leaf Southern Armyworm test, an individual lima bean leaf, *Phaseolus limensis* var. Woods' Prolific, was placed on moistened filter paper in a Petri dish (100×20 millimeters). The leaf was sprayed with the test solution using a rotating turntable sprayer and allowed to dry. The dish was infested with 10 third instar larvae of the Southern Armyworm and covered with the lid. If the larvae were alive two days after treatment, fresh untreated bean leaves were added. All treatments were maintained at 75°–80° F. under fluorescent light in a well ventilated room. Percent mortality was determined at two and four days after treatment.

The following tables exemplify, but do not limit, the preferred compounds of the present invention.

In Tables IA, IB and IC, the SAW (6 Day) column headings are the concentrations of the compounds of this invention at two different concentrations, 10 and 2.5 parts per million (ppm), and the observed percentage mortality for Southern Armyworm larvae at the listed concentration after 6 days using the whole plant test, unless noted otherwise.

TABLE IA

Compounds No. 1–72

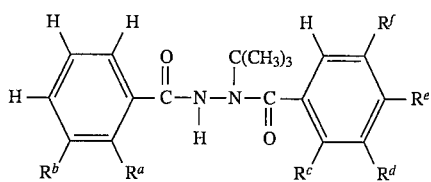

| Comp. No. | $R^a$ | $R^b$ | $R^c$ | $R^d$ | $R^e$ | $R^f$ | SAW (6 Day) 10 ppm | 2.5 ppm |
|---|---|---|---|---|---|---|---|---|
| 1 | CH$_3$ | OCH$_3$ | H | CH$_3$ | H | CH$_3$ | 100 | 100 |
| 2 | CH$_3$ | OCH$_3$ | H | CH$_3$ | H | H | NT[(1)] | 100 |
| 3 | CH$_3$ | OCH$_3$ | H | H | H | H | 100 | 100 |
| 4 | CH$_3$ | OCH$_3$ | Cl | H | Cl | H | NT | 100 |
| 5 | CH$_3$ | OCH$_3$ | Cl | H | H | CH$_3$ | NT | 100 |
| 6 | CH$_3$ | OCH$_3$ | Cl | H | H | H | 100 | 10 |
| 7 | CH$_3$ | OCH$_3$ | H | H | F | H | 100 | 100 |
| 8 | CH$_3$ | OCH$_3$ | H | H | Cl | H | NT | 100 |
| 9 | CH$_3$ | OCH$_3$ | Br | H | H | H | 100 | 0 |
| 10 | CH$_3$ | OCH$_3$ | Cl | H | F | H | 100 | 90 |
| 11 | CH$_3$ | OCH$_3$ | H | Cl | Cl | H | 100 | 100 |
| 12 | CH$_3$ | OCH$_3$ | H | Cl | H | Cl | 100 | 100 |
| 13 | CH$_3$ | OCH$_3$ | H | OCH$_3$ | H | H | 100 | 100 |
| 14 | CH$_3$ | OCH$_3$ | F | H | F | H | 100 | 20 |
| 15 | CH$_3$ | OCH$_3$ | OCH$_3$ | H | H | H | 100 | 30 |
| 16 | CH$_3$ | OCH$_3$ | H | H | CH$_3$ | H | 100 | 100 |
| 17 | CH$_3$ | OCH$_3$ | H | Cl | H | H | 100 | 100 |
| 18 | CH$_3$ | OCH$_3$ | H | CH$_3$ | CH$_3$ | H | NT | 100 |
| 19 | CH$_3$ | OCH$_3$ | H | F | H | F | 100 | 100 |
| 20 | CH$_3$ | OCH$_3$ | H | Br | H | H | 100 | 60 |
| 21 | CH$_3$ | OCH$_3$ | H | Cl | H | CH$_3$ | NT | 100 |
| 22 | CH$_3$ | OCH$_3$ | H | OCH$_3$ | H | CH$_3$ | NT | 100 |
| 23 | CH$_3$ | OCH$_3$ | H | OCH$_3$ | CH$_3$ | H | 100 | 100 |
| 24 | CH$_3$ | OCH$_3$ | H | CH$_3$ | Cl | H | 100 | 100 |
| 25 | CH$_3$ | OCH$_3$ | OCH$_3$ | H | Cl | H | 100 | 100 |
| 26 | CH$_3$ | OCH$_3$ | H | Br | H | CH$_3$ | NT | 100 |
| 27 | CH$_3$ | OCH$_3$ | H | Br | H | Cl | 100 | 100 |
| 28 | CH$_3$ | OCH$_3$ | H | Cl | F | H | 100 | 100 |
| 29 | CH$_3$ | OCH$_3$ | H | F | H | H | 100 | 100 |
| 30 | CH$_3$ | OCH$_3$ | H | F | F | H | 100 | 100 |
| 31 | CH$_3$ | OCH$_3$ | OCH$_3$ | H | CH$_3$ | H | NT | 100 |
| 32 | CH$_3$ | OCH$_3$ | H | Cl | Cl | Cl | 100 | 100 |
| 33 | CH$_3$ | OCH$_3$ | H | F | F | F | 100 | 100 |
| 34 | CH$_3$ | OCH$_3$ | H | OCH$_3$ | CH$_3$ | OCH$_3$ | 100 | 100 |
| 35 | CH$_3$ | OCH$_3$ | OCH$_3$ | H | H | OCH$_3$ | 100 | 0 |
| 36 | Br | OCH$_3$ | H | CH$_3$ | H | CH$_3$ | NT | 100 |
| 37 | Cl | OCH$_3$ | H | CH$_3$ | H | CH$_3$ | NT | 100 |
| 38 | CH$_3$ | OCF$_3$ | H | CH$_3$ | H | CH$_3$ | NT | 100 |
| 39 | CH$_3$ | OC$_2$H$_5$ | H | CH$_3$ | H | CH$_3$ | NT | 100 |
| 40 | CH$_3$ | OCH$_3$ | H | —OCH$_2$O— | | H | 100 | 10 |
| 41 | CH$_3$ | OCH$_3$ | OCH$_3$ | H | H | CH$_3$ | 100 | 70 |
| 42 | CH$_3$ | OCH$_3$ | NO$_2$ | H | H | H | 100 | 10 |
| 43 | CH$_3$ | OCH$_3$ | H | OCH$_3$ | H | OCH$_3$ | 100 | 100 |
| 44 | CH$_3$ | OCH$_3$ | OCH$_3$ | H | H | Cl | 100 | 10 |
| 45 | CH$_3$ | OCH$_3$ | CH$_3$ | H | CH$_3$ | H | 100 | 50 |
| 46 | CH$_3$ | OCH$_3$ | H | Br | F | H | NT | 100 |
| 47 | CH$_3$ | OCH$_3$ | H | F | CH$_3$ | H | NT | 100 |
| 48 | CH$_3$ | OCH$_3$ | H | Br | OCH$_3$ | Br | 100 | NT |
| 49 | CH$_3$ | OCH$_3$ | F | F | F | H | 100 | 10 |
| 50 | CH$_3$ | OCH$_3$ | H | Cl | CH$_3$ | H | NT | 100 |
| 51 | CH$_3$ | OCH$_3$ | H | Cl | OCH$_3$ | H | 100 | 100 |
| 52 | CH$_3$ | OCH$_3$ | H | C$_2$H$_5$ | H | H | 100 | 100 |
| 53 | CH$_3$ | OCH$_3$ | H | Cl | F | Cl | 100 | 100 |
| 54 | C$_2$H$_5$ | OCH$_3$ | H | CH$_3$ | H | CH$_3$ | 100 | 100 |
| 55 | C$_2$H$_5$ | OCH$_3$ | H | Cl | H | CH$_3$ | 100 | 100 |
| 56 | C$_2$H$_5$ | OCH$_3$ | OCH$_3$ | H | H | H | 100 | 80 |
| 57 | C$_2$H$_5$ | OCH$_3$ | H | F | H | F | 100 | 100 |
| 58 | C$_2$H$_5$ | OCH$_3$ | H | OCH$_3$ | H | H | 100 | 100 |
| 59 | C$_2$H$_5$ | OCH$_3$ | H | CH$_3$ | H | H | 100 | 100 |
| 60 | C$_2$H$_5$ | OCH$_3$ | Cl | H | H | H | 100 | 50 |
| 61 | C$_2$H$_5$ | OCH$_3$ | H | Cl | H | Cl | 100 | 100 |
| 62 | CH$_3$ | OCH$_3$ | H | CH$_2$OCH$_3$ | H | CH$_3$ | 100 | 10 |
| 63 | C$_2$H$_5$ | OCH$_3$ | Cl | H | Cl | H | 100 | 100 |
| 64 | CH$_3$ | OCH$_3$ | H | OC$_2$H$_5$ | H | H | 100 | 10 |

TABLE IA-continued

Compounds No. 1–72

[Structure: N-(2-R^a-3-R^b-benzoyl)-N'-(2-R^c-3-R^d-4-R^e-R^f-benzoyl)-N'-C(CH3)3-hydrazine]

| Comp. No. | $R^a$ | $R^b$ | $R^c$ | $R^d$ | $R^e$ | $R^f$ | SAW (6 Day) 10 ppm | SAW (6 Day) 2.5 ppm |
|---|---|---|---|---|---|---|---|---|
| 65 | $C_2H_5$ | $OCH_3$ | Cl | H | H | $CH_3$ | 100 | 100 |
| 66 | $CH_3$ | $OCH_3$ | $NO_2$ | H | H | $CH_3$ | 100 | 90 |
| 67 | Cl | $OCH_3$ | H | $CH_3$ | H | H | NT | 100[2] |
| 68 | Cl | $OCH_3$ | H | H | H | H | NT | 80[2] |
| 69 | Cl | $OCH_3$ | Cl | H | Cl | H | NT | 70[2] |
| 70 | Cl | $OCH_3$ | Cl | H | H | $CH_3$ | 100 | 10 |
| 71 | Cl | $OCH_3$ | $CH_3$ | H | $CH_3$ | H | 100 | 100 |
| 72 | $C_2H_5$ | $OC_2H_5$ | H | $CH_3$ | H | $CH_3$ | 100 | 40 |

[1] NT indicates the compound was not tested at the particular concentration.
[2] Tested using detached leaf method; observations made after 4 days.

TABLE IB

Compounds No. 73–78

[Structure with $(CH_2)_n$ dioxy ring]

| Compound Number | $R^a$ | n | SAW (6 Day) 10 ppm | SAW (6 Day) 2.5 ppm |
|---|---|---|---|---|
| 73 | $CH_3$ | 1 | 100 | 100 |
| 74 | $C_2H_5$ | 1 | 100 | 100 |
| 75 | Cl | 1 | 100 | 100 |
| 76 | Br | 1 | 100 | 100 |
| 77 | $CH_3$ | 2 | 100 | 100 |
| 78[2] | $C_2H_5$ | 2 | 100 | 100 |

[2] Tested using detached leaf method; observations made after 4 days.

TABLE IC

Compound No. 79

[Structure]

| SAW (6 Day) 10 ppm | 2.5 ppm |
|---|---|
| 100 | 100 |

In Table II, the PLH (3 Day) column heading is the observed percentage mortality for the Potato Leafhopper when treated with a compound of the present invention at a concentration of 10 ppm.

TABLE II

Results of Testing on Potato Leafhopper

| Compound Number | PLH (3 Day) at 10 ppm |
|---|---|
| 54 | 100 |
| 55 | 100 |
| 56 | 100 |
| 58 | 80 |
| 59 | 100 |
| 60 | 90 |
| 72 | 60 |
| 77 | 90 |
| 78 | 90 |

It should be understood that the instant specification and examples are set forth by way of illustration and not limitation, and that various modifications and changes may be made without departing from the spirit and scope of the present invention as defined by the appended claims.

We claim:

1. An insecticidal compound having the formula N-(2-$R^a$-3-$R^b$-4-$R^h$-benzoyl)-N'-(2-$R^c$-3-$R^d$-4-$R^e$-5-$R^f$-benzoyl)-N'-$R^g$-hydrazine wherein $R^a$ is a halo or lower alkyl; $R^b$ is lower alkoxy; $R^c$ is selected from hydrogen, halo and lower alkyl; $R^d$, $R^e$ and $R^f$ are each independently selected from hydrogen, bromo, chloro, fluoro and lower alkyl; $R^g$ is a $(C_4-C_6)$alkyl; $R^h$ is hydrogen or lower alkyl.

2. The insecticidal compound of claim 1 wherein $R^a$ is bromo, chloro, or $(C_1-C_3)$alkyl; $R^b$ is $(C_1-C_4)$alkoxy; $R^c$ is selected from hydrogen, bromo, chloro, fluoro and $(C_1-C_3)$alkyl; $R^d$, $R^e$ and $R^f$ are each independently selected from hydrogen, bromo, chloro, fluoro, $(C_1-C_3)$alkyl, $(C_1-C_4)$alkoxy, and $(C_1-C_2)$alkoxy$(C_1-C_2)$alkyl; $R^g$ is a $(C_4-C_6)$alkyl; $R^h$ is hydrogen or $(C_1-C_2)$alkyl.

3. The insecticidal compound of claim 2 wherein $R^a$ is bromo, chloro, methyl or ethyl; $R^b$ is methoxy or ethoxy; $R^c$, $R^d$, $R^e$ and $R^f$ are each independently selected from hydrogen, bromo, chloro, fluoro and methyl; $R^g$ is tert butyl, neopentyl or methylneopentyl.

4. The insecticidal compound of claim 3 wherein $R^a$ is methyl or ethyl; $R^b$ is methoxy or ethoxy; $R^c$, $R^d$, $R^e$, and $R^f$ are each independently selected from hydrogen, bromo, chloro, fluoro and methyl; $R^g$ is tert-butyl; and $R^h$ is hydrogen.

5. The insecticidal compound of claim 4 wherein $R^b$ is methoxy and no more than three of $R^c$, $R^d$, $R^e$, and $R^f$ are the same member selected from a group consisting of bromo, chloro, fluoro and methyl.

6. The insecticidal compound of claim 5 wherein no more than three of $R^c$, $R^d$, $R^e$, and $R^f$ are independently selected from chloro, fluoro and methyl with the remaining $R^c$, $R^d$, $R^e$ and $R^f$ being hydrogen.

7. The insecticidal compound of claim 6 wherein $R^d$ and $R^f$ are independently selected from chloro and methyl and $R^c$ and $R^e$ are both hydrogen.

8. The insecticidal compound of claim 7 wherein $R^d$ and $R^f$ are each independently selected from bromo, chloro, and fluoro.

9. The insecticidal compound of claim 8 wherein $R^d$ and $R^f$ are each chloro.

10. The insecticidal compound of claim 7 wherein $R^d$ and $R^f$ are methyl.

11. The insecticidal compound of claim 7 wherein $R^d$ is selected from bromo, chloro, and fluoro, and $R^f$ is methyl.

12. The insecticidal compound of claim 11 wherein $R^d$ is chloro and $R^f$ is methyl.

13. The insecticidal compound of claim 5 wherein $R^c$ is selected from chloro and fluoro; and $R^d$ is hydrogen.

14. The insecticidal compound of claim 13 wherein $R^c$ is chloro and $R^f$ is methyl.

15. The insecticidal compound of claim 5 wherein $R^c$ is chloro and $R^d$ is chloro.

16. The insecticidal compound of claim 4 wherein $R^c$ is hydrogen, $R^d$ is hydrogen, $R^e$ is chloro, and $R^f$ is hydrogen.

17. The insecticidal compound of claim 4 wherein $R^c$ is hydrogen, $R^d$ is methyl, $R^e$ is hydrogen, and $R^f$ is hydrogen.

18. The insecticidal compound of claim 4 wherein $R^c$ is hydrogen, $R^d$ is hydrogen, $R^e$ is hydrogen, and $R^f$ is hydrogen.

19. The insecticidal compound of claims 1 or 2 which is selected from

N-(3-methoxy-2-methylbenzoyl)-N'-(3-chloro-5-methylbenzoyl)-N'-tert-butylhydrazine, N-(3-methoxy-2-methylbenzoyl)-N'-(3,5-dimethylbenzoyl)-N'-tert-butylhydrazine, N-(3-methoxy-2-methylbenzoyl)-N'-(3,5-dichlorobenzoyl)-N'-tert-butylhydrazine, N-(3-methoxy-2-methylbenzoyl)-N'-(2,4-dichlorobenzoyl)-N'-tert-butylhydrazine, N-(3-methoxy-2-methylbenzoyl)-N'-(3-methylbenzoyl)-N'-tert-butylhydrazine, N-(3-methoxy-2-methylbenzoyl)-N'-benzoyl-N'-tert-butylhydrazine, N-(3-methoxy-2-methylbenzoyl)-N'-(4-chlorobenzoyl)-N'-tert-butylhydrazine, N-(3-methoxy-2-methylbenzoyl)-N'-(3,4,5-trichlorobenzoyl)- N'-tert-butylhydrazine, N-(3-methoxy-2-methylbenzoyl)-N'-(3,4-dichlorobenzoyl)-N'-tert-butylhydrazine, N-(3-methoxy-2-methylbenzoyl)-N'-(4-fluorobenzoyl)-N'-tert-butylhydrazine, N-(3-methoxy-2-methylbenzoyl)-N'-(3,4-dimethylbenzoyl)- N'-tert-butylhydrazine, N-(3-methoxy-2-methylbenzoyl)-N'-(4-chloro-3-methylbenzoyl)-N'-tert-butylhydrazine, N-(3-methoxy-2-methylbenzoyl)-N'-(3-bromo-5-methylbenzoyl)-N'-tert-butylhydrazine, N-(3-methoxy-2-methylbenzoyl)-N'-(3-bromo-5-chlorobenzoyl)-N'-tert-butylhydrazine, N-(3-methoxy-2-methylbenzoyl)-N'-(3,5-difluorobenzoyl)-N'-tert-butylhydrazine, N-(3-methoxy-2-methylbenzoyl)-N'-(4-methylbenzoyl)-N'-tert-butylhydrazine, N-(3-methoxy-2-methylbenzoyl)-N'-(3-chloro-4-fluorobenzoyl)-N'-tert-butylhydrazine, N-(3-methoxy-2-methylbenzoyl)-N'-(3-fluorobenzoyl)-N'-tert-butylhydrazine, N-(3-methoxy-2-methylbenzoyl)-N'-(3,4-difluorobenzoyl)-N'-tert-butylhydrazine, N-(3-methoxy-2-methylbenzoyl)-N'-(3,5-dimethylbenzoyl)- N'-tert-butylhydrazine, N-(3-methoxy-2-methylbenzoyl)-N'-(3-chlorobenzoyl)-N'-tert-butylhydrazine, N-(3-methoxy-2-methylbenzoyl)-N'-(2-chloro-5-methylbenzoyl)-N'-tert-butylhydrazine, N-(2-bromo-3-methoxybenzoyl)-N'-(3,5-dimethylbenzoyl)-N'-tert-butylhydrazine, N-(2-chloro-3-methoxybenzoyl)-N'-(3,5-dimethylbenzoyl)-N'-tert-butylhydrazine, N-(3-methoxy-2-methylbenzoyl)-N'-(3-bromo-4-fluorobenzoyl)-N'-tert-butylhydrazine, N-(3-methoxy-2-methylbenzoyl)-N'-(4-fluoro-3-methylbenzoyl)-N'-tert-butylhydrazine, N-(3-methoxy-2-methylbenzoyl)-N'-(3-chloro-4-methylbenzoyl)-N'-tert-butylhydrazine, N-(3-methoxy-2-methylbenzoyl)-N'-(3-ethylbenzoyl)-N'-tert-butylhydrazine, N-(3-methoxy-2-methylbenzoyl)-N'-(2,5-dichloro-4-fluorobenzoyl)-N'-tert-butylhydrazine, N-(2-ethyl-3-methoxybenzoyl)-N'-(3,5-dimethylbenzoyl)-N'-tert-butylhydrazine, N-(2-ethyl-3-methoxybenzoyl)-N'-(3-chloro-5-methylbenzoyl)-N'-tert-butylhydrazine, N-(2-ethyl-3-methoxybenzoyl)-N'-(2,5-difluorobenzoyl)-N'-tert-butylhydrazine, N-(2-ethyl-3-methoxybenzoyl)-N'-(3-methylbenzoyl)-N'-tert-butylhydrazine, N-(2-ethyl-3-methoxybenzoyl)-N'-(3,5-dichlorobenzoyl)-N'- tert-butylhydrazine, N-(2-ethyl-3-methoxybenzoyl)-N'-(2,4-dichlorobenzoyl)-N'-tert-butylhydrazine, N-(2-ethyl-3-methoxybenzoyl)-N'-(2-chloro-5-methylbenzoyl)-N'-tert-butylhydrazine, N-(3-ethoxy-2-ethylbenzoyl)-N'-(3,5-dimethylbenzoyl)-N'-tert-butylhydrazine, N-(3-methoxy-2-methylbenzoyl)-N'-(3,5-dimethylbenzoyl)-N'neopentylhydrazine, N-(3-methoxy-2-methylbenzoyl)-N'-(3,5-dimethylbenzoyl)-N'(methylneopentyl)hydrazine N-(2-ethyl-3-methoxybenzoyl)-N'-(3,5-dimethylbenzoyl)-N'-neopentylhydrazine, and N-(2-ethyl-3-methoxybenzoyl)-N'-(3,5-dimethylbenzoyl)-N'-(methylneopentyl)hydrazine.

20. An insecticidal composition comprising one or more compounds having the formula N-(2-$R^a$-3-$R^b$-4-$R^h$-benzoyl)-N'-(2-$R^c$-3-$R^d$- 4-$R^e$-5$R^f$-benzoyl)-N'-$R^g$-hydrazine wherein $R^a$ is a halo or lower alkyl; $R^b$ is lower alkoxy; $R^c$ is selected from hydrogen, halo and lower alkyl; $R^d$, $R^e$ and $R^f$ are each independently selected from hydrogen, bromo, chloro, fluoro and lower alkyl; $R^g$ is a ($C_4$–$C_6$)alkyl; $R^h$ is hydrogen or lower alkyl.

21. The insecticidal composition of claim 20 which is used to control insects of the order Lepidoptera.

22. The insecticidal composition of claim 21 comprising one or more compounds which are selected from N-(3-methoxy-2-methylbenzoyl)-N'-(3-chloro-5-methylbenzoyl)-N'-tert-butylhydrazine, N-(3-methoxy-2-methylbenzoyl)-N'-(3,5-dimethylbenzoyl)-N'-tert-butylhydrazine, N-(3-methoxy-2-methylbenzoyl)-N'-(3-methylbenzoyl)-N'-tert-butylhydrazine, N-(3-methoxy-2-methylbenzoyl)-N'-(3,5-dichlorobenzoyl)-N'-tert-butylhydrazine, N-(3-methoxy-2-methylbenzoyl)-N'-(3,4-dichlorobenzoyl)-N'-tert-butylhydrazine, N-(3-methoxy-2-methylbenzoyl)-N'-(4-fluorobenzoyl)-N'-tert-butylhydrazine, N-(3-methoxy-2-methylbenzoyl)-N'-(3,4-dimethylbenzoyl)-N'-tert-butylhydrazine, N-(3-methoxy-2-methylbenzoyl)-N'-(4-chloro-3-methylbenzoyl)-N'-tert-butylhydrazine, N-(3-methoxy-2-methylbenzoyl)-N'-(3-bromo-5-methylbenzoyl)-N'-tert-butylhydrazine, N-(3-methoxy-2-methylbenzoyl)-N'-(4-chlorobenzoyl)-N'-tert-butylhydrazine, N-(3-methoxy-2-methylbenzoyl)-N'-(3-bromo-5-chlorobenzoyl)-N'-tert-butylhydrazine, N-(3-methoxy-2-methylbenzoyl)-N'-(3,5-difluorobenzoyl)-N'-tert-butylhydrazine, N-(3-methoxy-2-methylbenzoyl)-N'-(4-methylbenzoyl)-N'-tert-butylhydrazine, N-(3-methoxy-2-methylbenzoyl)-N'-(3-chloro-4-fluorobenzoyl)-N'-tert-butylhydrazine, N-(3-methoxy-2-methylbenzoyl)-N'-(3-fluorobenzoyl)-N'-tert-butylhydrazine, N-(3-methoxy-2-methylbenzoyl)-N'-(3,4-difluorobenzoyl)-N'-tert-butylhydrazine, N-(3-methoxy-2-methylbenzoyl)-N'-(2,4-dichlorobenzoyl)-N'-tert-butylhydrazine, N-(3-ethoxy-2-methylbenzoyl)-N'-(3,5-dimethylbenzoyl)-N'-tert-butylhydrazine, N-(3-methoxy-2-methylbenzoyl)-N'-(3-chlorobenzoyl)-N'-tert-butylhydrazine, N-(3-methoxy-2-methylbenzoyl)-N'-(3,5-dimethylbenzoyl)-N'-neopentylhydrazine, N-(2-bromo-3-methoxybenzoyl)-N'-(3,5-dimethylbenzoyl)-N'-tert-butylhydrazine, N-(2-chloro-3-methoxybenzoyl)-N'-(3,5-dimethylbenzoyl)-N'-tert-butylhydrazine, N-(3-methoxy-2-methylbenzoyl)-N'-(4-methylbenzoyl)-N'-tert-butylhydrazine, N-(3-methoxy-2-methylbenzoyl)-N'-(3-bromo-4-fluorobenzoyl)-N'-tert-butylhydrazine, N-(3-methoxy-2-methylbenzoyl)-N'-(3-fluoro-4-methylbenzoyl)-N'-tert-butylhydrazine, N-(3-methoxy-2-methylbenzoyl)-N'-(3-chloro-4-methylbenzoyl)-N'-tert-butylhydrazine, N-(3-methoxy-2-methylbenzoyl)-N'-(3,4,5-trichlorobenzoyl)-N'-tert-butylhydrazine, N-(3-methoxy-2-methylbenzoyl)-N'-(3-ethylbenzoyl)-N'-tert-butylhydrazine, N-(3-methoxy-2-methylbenzoyl)-N'-(3,5-dichloro-4-fluorobenzoyl)-N'-tert-butylhydrazine, N-(2-ethyl-3-methoxybenzoyl)-N'-(3,5-dimethylbenzoyl)-N'-tert-butylhydrazine, N-(2-ethyl-3-methoxybenzoyl)-N'-(3-chloro-5-methylbenzoyl)-N'-tert-butylhydrazine, N-(2-ethyl-3-methoxybenzoyl)-N'-(3,5-difluorobenzoyl)-N'-tert-butylhydrazine, N-(2-ethyl-3-methoxybenzoyl)-N'-(3-methylbenzoyl)-N'-tert-butylhydrazine, N-(2-ethyl-3-methoxybenzoyl)-N'-(3,5-dichlorobenzoyl)-N'-tert-butylhydrazine, N-(2-ethyl-3-methoxybenzoyl)-N'-(2,4-dichlorobenzoyl)-N'-tert-butylhydrazine, N-(2-ethyl-3-methoxybenzoyl)-N'-(2-chloro-5-methylbenzoyl)-N'-tert-butylhydrazine, N-(2-chloro-3-methoxybenzoyl)-N'-(3,5-dimethylbenzoyl)-N'-tert-butylhydrazine, and N-(2-bromo-3-methoxybenzoyl)-N'-(3,5-dimethylbenzoyl)-N'-tert-butylhydrazine.

23. The insecticidal composition of claim 22 comprising one or more compounds which are selected from N-(3-methoxy-2-methylbenzoyl)-N'-(3-chloro-5-methylbenzoyl)-N'-tert-butylhydrazine, N-(3-methoxy-2-methylbenzoyl)-N'-(3,5-dimethylbenzoyl)-N'-tert-butylhydrazine, N-(3-ethoxy-2-methylbenzoyl)-N'-(3,5-dimethylbenzoyl)-N'-tert-butylhydrazine, N-(3-methoxy-2-methylbenzoyl)-N'-(3-methylbenzoyl)-N'-tert-butylhydrazine, N-(3-methoxy-2-methylbenzoyl)-N'-(3,5-dichlorobenzoyl)-N'-tert-butylhydrazine, N-(3-methoxy-2-methylbenzoyl)-N'-(3,4-dichlorobenzoyl)-N'-tert-butylhydrazine, N-(3-methoxy-2-methylbenzoyl)-N'-(4-fluorobenzoyl)-N'-tert-butylhydrazine, N-(2-chloro-3-methoxybenzoyl)-N'-(3,5-dimethylbenzoyl)-N'-tert-butylhydrazine and N-(2-bromo-3-methoxybenzoyl)-N'-(3,5-dimethylbenzoyl)-N'-tert-butylhydrazine.

24. The insecticidal composition of claim 20 which is used to control insects of the order Homoptera.

25. The insecticidal composition of claim 24 comprising one or more compounds which are selected from N-(2-ethyl-3-methoxybenzoyl)-N'-(3,5-dimethylbenzoyl)-N'-tert-butylhydrazine, N-(2-ethyl-3-methoxybenzoyl)-N'-(3-chloro-5-methylbenzoyl)-N'-tert-butylhydrazine, N-(2-ethyl-3-methoxybenzoyl)-N'-(2-chlorobenzoyl)-N'-tert-butylhydrazine, N-(2-ethyl-3-methoxybenzoyl)-N'-(3-methylbenzoyl)-N'-tert-butylhydrazine and N-(3-ethoxy-2-ethylbenzoyl)-N'-(3,5-dimethylbenzoyl)-N'-tert-butylhydrazine.

26. A method for controlling insects comprising contacting the insect with an insecticidally effective amount of a compound having the formula N-(2-$R^a$-3-$R^b$-4-$R^h$-benzoyl)-N'-(2-$R^c$-3-$R^d$-4-$R^e$-5-$R^f$-benzoyl)-N'-$R^g$-hydrazine wherein $R^a$ is a halo or lower alkyl; $R^b$ is lower alkoxy; $R^c$ is selected from hydrogen, halo and lower alkyl; $R^d$, $R^e$ and $R^f$ are each independently selected from hydrogen, bromo, chloro, fluoro and lower alkyl; $R^g$ is a $(C_4-C_6)$alkyl; $R^h$ is hydrogen or lower alkyl.

27. The method of claim 26 which is used to control insects of the order Lepidoptera.

28. The method of claim 27 comprising one or more compounds which are selected from N-(3-methoxy-2-methylbenzoyl)-N'-(3-chloro-5-methylbenzoyl)-N'-tert-butylhydrazine, N-(3-methoxy-2-methylbenzoyl)-N'-(3,5-dimethylbenzoyl)-N'-tert-butylhydrazine, N-(3-methoxy-2-methylbenzoyl)-N'-(3-methylbenzoyl)-N'-tert-butylhydrazine, N-(3-methoxy-2-methylbenzoyl)-N'-(3,5-dichlorobenzoyl)-N'-tert-butylhydrazine, N-(3-methoxy-2-methylbenzoyl)-N'-(3,4-dichlorobenzoyl)-N'-tert-butylhydrazine, N-(3-methoxy-2-methylbenzoyl)-N'-(4-fluorobenzoyl)-N'-tert-butylhydrazine, N-(3-methoxy-2-methylbenzoyl)-N'-(3,4-dimethylbenzoyl)-N'-tert-butylhydrazine, N-(3-methoxy-2-methylbenzoyl)-N'-(4-chloro-3-methylbenzoyl)-N'-tert-butylhydrazine, N-(3-methoxy-2-methylbenzoyl)-N'-(3-bromo-5-methylbenzoyl)-N'-tert-butylhydrazine, N-(3-methoxy-2-methylbenzoyl)-N'-(4-chlorobenzoyl)-N'-tert-butylhydrazine, N-(3-methoxy-2-methylbenzoyl)-N'-(3-bromo-5-chlorobenzoyl)-N'-tert-butylhydrazine, N-(3-methoxy-2-methylbenzoyl)-N'-(3,5-difluorobenzoyl)-N'-tert-butylhydrazine, N-(3-methoxy-2-methylbenzoyl)-N'-(4-methylbenzoyl)-N'-tert-butylhydrazine, N-(3-methoxy-2-methylbenzoyl)-N'-(3-chloro-4-fluorobenzoyl)-N'-tert-butylhydrazine, N-(3-methoxy-2-methylbenzoyl)-N'-(3-fluorobenzoyl)-N'-tert-butylhydrazine, N-(3-methoxy-2-methylbenzoyl)-N'-(3,4-difluorobenzoyl)-N'-tert-butylhydrazine, N-(3-methoxy-2-methylbenzoyl)-N'-(2,4-dichlorobenzoyl)-N'-tert-butylhydrazine, N-(3-ethoxy-2-methylbenzoyl)-N'-(3,5-dimethylbenzoyl)-N'-tert-butylhydrazine, N-(3-methoxy-2-methylbenzoyl)-N'-(3-chlorobenzoyl)-N'-tert-butylhydrazine, N-(3-methoxy-2-methylbenzoyl)-N'-(3,5-dimethylbenzoyl)-N'-neopentylhydrazine, N-(2-bromo-3-methoxybenzoyl)-N'-(3,5-dimethylbenzoyl)-N'-tert-butylhydrazine, N-(2-chloro-3-methoxybenzoyl)-N'-(3,5-dimethylbenzoyl)-N'-tert-butylhydrazine, N-(3-methoxy-2-methylbenzoyl)-N'-(4-methylbenzoyl)-N'-tert-butylhydrazine, N-(3-methoxy-2-methylbenzoyl)-N'-(3-bromo-4-fluorobenzoyl)-N'-tert-butylhydrazine, N-(3-methoxy-2-methylbenzoyl)-N'-(3-fluoro-4-methylbenzoyl)-N'-tert-butylhydrazine, N-(3-methoxy-2-methylbenzoyl)-N'-(3-chloro-4-methylbenzoyl)-N'-tert-butylhydrazine, N-(3-methoxy-2-methylbenzoyl)-N'-(3,4,5-trichlorobenzoyl)-N'-tert-butylhydrazine, N-(3-methoxy-2-methylbenzoyl)-N'-(3-ethylbenzoyl)-N'-tert-butylhydrazine, N-(3-methoxy-2-methylbenzoyl)-N'-(3,5-dichloro-4-fluorobenzoyl)-N'-tert-butylhydrazine, N-(2-ethyl-3-methoxybenzoyl)-N'-(3,5-dimethylbenzoyl)-N'-tert-butylhydrazine, N-(2-ethyl-3-methoxybenzoyl)-N'-(3-chloro-5-methylbenzoyl)-N'-tert-butylhydrazine, N-(2-ethyl-3-methoxybenzoyl)-N'-(3,5-difluorobenzoyl)-N'-tert-butylhydrazine, N-(2-ethyl-3-methoxybenzoyl)-N'-(3-methylbenzoyl)-N'-tert-butylhydrazine, N-(2-ethyl-3-methoxybenzoyl)-N'-(3,5-dichlorobenzoyl)-N'-tert-butylhydrazine, N-(2-ethyl-3-methoxybenzoyl)-N'-(2,4-dichlorobenzoyl)-N'-tert-butylhydrazine.

N-(2-ethyl-3-methoxybenzoyl)-N'-(2-chloro-5-methylbenzoyl)-N'-tert-butylhydrazine, N-(2-chloro-3-methoxybenzoyl)-N'-(3,5-dimethylbenzoyl)-N'-tert-butylhydrazine and N-(2-bromo-3-methoxybenzoyl)-N'-(3,5-dimethylbenzoyl)-N'-tert-butylhydrazine.

29. The method of claim 28 comprising one or more compounds which are selected from N-(3-methoxy-2-methylbenzoyl)-N'-(3-chloro-5-methylbenzoyl)-N'-tert-butylhydrazine, N-(3-methoxy-2-methylbenzoyl)-N'-(3,5-dimethylbenzoyl)-N'-tert-butylhydrazine, N-(3-ethoxy-2-methylbenzoyl)-N'-(3,5-dimethylbenzoyl)-N'-tert-butylhydrazine, N-(3-methoxy-2-methylbenzoyl)-N'-(3-methylbenzoyl)-N'-tert-butylhydrazine, N-(3-methoxy-2-methylbenzoyl)-N'-(3,5-dichlorobenzoyl)-N'-tert-butylhydrazine, N-(3-methoxy-2-methylbenzoyl)-N'-(3,4-dichlorobenzoyl)-N'-tert-butylhydrazine, N-(3-methoxy-2-methylbenzoyl)-N'-(4-fluorobenzoyl)-N'-tert-butylhydrazine, N-(2-chloro-3-methoxybenzoyl)-N'-(3,5-dimethylbenzoyl)-N'-tert-butylhydrazine and N-(2-bromo-3-methoxybenzoyl)-N'-(3,5-dimethylbenzoyl)-N'-tert-butylhydrazine.

30. The method of claim 26 which is used to control insects of the order Homoptera.

31. The method of claim 30 comprising one or more compounds which are selected,d from N-(2-ethyl-3-methoxybenzoyl)-N'-(3,5-dimethylbenzoyl)-N'-tert-butylhydrazine, N-(2-ethyl-3-methoxybenzoyl)-N'-(3-chloro-5-methylbenzoyl)-N'-tert-butylhydrazine, N-(2-ethyl-3-methoxybenzoyl)-N'-(2-chlorobenzoyl)-N'-tert-butylhydrazine, N-(3-ethoxy-2-ethylbenzoyl)-N'-(3,5-dimethylbenzoyl)-N'-tert-butylhydrazine and N-(2-ethyl-3-methoxybenzoyl)-N'-(3-methylbenzoyl)-N'-tert-butylhydrazine.

* * * * *